(12) United States Patent
Cance et al.

(10) Patent No.: US 9,394,253 B2
(45) Date of Patent: Jul. 19, 2016

(54) KINASE PROTEIN BINDING INHIBITORS

(71) Applicant: Roswell Park Cancer Institute, Buffalo, NY (US)

(72) Inventors: William G. Cance, Orchard Park, NY (US); Ravindra K. Pandey, East Amherst, NY (US); Elena V. Kurenova, West Falls, NY (US); Manivannan Ethirajan, Cheektowaga, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 13/261,870

(22) PCT Filed: Nov. 13, 2012

(86) PCT No.: PCT/US2012/064819
§ 371 (c)(1),
(2) Date: May 14, 2014

(87) PCT Pub. No.: WO2013/074517
PCT Pub. Date: May 23, 2013

(65) Prior Publication Data
US 2015/0051245 A1    Feb. 19, 2015

Related U.S. Application Data

(60) Provisional application No. 61/559,517, filed on Nov. 14, 2011.

(51) Int. Cl.
| | | |
|---|---|---|
| C07D 213/74 | (2006.01) |
| C07D 215/38 | (2006.01) |
| C07D 207/34 | (2006.01) |
| C07D 209/40 | (2006.01) |
| C07C 211/45 | (2006.01) |
| A61K 45/06 | (2006.01) |
| A61K 31/337 | (2006.01) |
| A61K 31/4188 | (2006.01) |
| A61K 31/513 | (2006.01) |
| A61K 31/7048 | (2006.01) |
| A61K 31/7068 | (2006.01) |
| A61K 33/24 | (2006.01) |

(52) U.S. Cl.
CPC ............ *C07D 215/38* (2013.01); *A61K 31/337* (2013.01); *A61K 31/4188* (2013.01); *A61K 31/513* (2013.01); *A61K 31/7048* (2013.01); *A61K 31/7068* (2013.01); *A61K 33/24* (2013.01); *A61K 45/06* (2013.01); *C07C 211/45* (2013.01); *C07D 207/34* (2013.01); *C07D 209/40* (2013.01); *C07D 213/74* (2013.01)

(58) Field of Classification Search
None
See application file for complete search history.

(56) References Cited

U.S. PATENT DOCUMENTS

2011/0201687 A1    8/2011   Kobayashi et al.

FOREIGN PATENT DOCUMENTS

| GB | 606181 | * | 8/1948 |
| WO | WO-0206235 A1 | | 1/2002 |
| WO | WO-2004013235 A1 | | 2/2004 |
| WO | WO-2009146696 A1 | | 12/2009 |
| WO | WO-2011075688 A1 | | 6/2011 |

OTHER PUBLICATIONS

Rao et al, Journal of Pharmacology and Experimental Therapeutics (1975), 195(3), pp. 433-440.*
International Search Report of PCT/US2012/064819, dated Mar. 29, 2013.
International Preliminary Report on Patentability for PCT/US2012/064819 dated May 20, 2014.
Written Opinion for PCT/US2012/064819 dated Mar. 29, 2013.

* cited by examiner

*Primary Examiner* — Zinna Northington Davis
(74) *Attorney, Agent, or Firm* — Bryan D. Zerhusen; Locke Lord LLP

(57) ABSTRACT

The invention relates to protein binding inhibitor compounds and methods of identifying and using them. The invention further relates to pharmaceutical compositions and methods for treating cell proliferative disorders, especially cancer.

1 Claim, 16 Drawing Sheets

| Compound | C4 | C10 | C9 | C1 |
|---|---|---|---|---|
| Grid score | 30.49 | 36.94 | 46.12 | 24.84 |
| KD (M) | 100μM: 5.7 x 10$^{-7}$ | 20μM: 6.94 x 10$^{-8}$ | 20μM: 1.47 x 10$^{-7}$ | Does not bind |

FAT domain of FAK
Carbon chain
Nitrogen residues

KINASE PROTEIN BINDING INHIBITORS

CROSS-REFERENCE TO RELATED APPLICATION

This application is the national phase under 35 U.S.C. §371 of PCT International Application No. PCT/US2012/064819, filed Nov. 13, 2012, which claims the benefit of Provisional Patent Application No. 61/559,517, filed Nov. 14, 2011, the entire contents of the aforementioned applications are hereby incorporated herein by reference.

STATEMENT OF RIGHTS TO INVENTIONS MADE UNDER FEDERALLY SPONSORED RESEARCH

This invention was made with government support under CA065910 awarded by the National Institutes of Health. The government has certain rights in the invention.

BACKGROUND OF THE INVENTION

Focal Adhesion Kinase (FAK) is an important survival molecule that is upregulated in a broad range of solid tumors and is expressed at very low levels in normal tissues, creating a therapeutic window and making this protein a highly attractive target for the treatment of cancer, as suggested by our lab [1] and recently by other leading authors in the field [2, 3]. See also WO 2005/049852, the contents of which are incorporated by reference. We have identified the key-binding partners of FAK and peptides from the binding sites that cause apoptosis in cancer but not normal cells. Based on these findings as well as correlative structural and functional data, we suggest that blocking FAK-protein interactions will lead to apoptosis and tumor cell death. We have well-documented data that targeting FAK interactions is important for cell survival, and we have used atomic resolution structural data of specific binding sites to identify small molecule lead compounds. We have screened small molecule libraries and identified several lead compounds that disrupt binding of FAK to key signaling molecules and induce apoptosis in breast, colon, pancreatic, lung, as well as melanoma cancer cell lines. Some of these compounds caused apoptosis at low nanomolar concentrations. We also have shown that lead compounds increase the sensitivity of cancer cells to standard chemotherapy drugs.

Our data suggest that peptides and small molecule inhibitors of FAK can be identified as lead compounds to provide the basis for targeted novel cancer therapeutic agents. Such compounds will effectively reduce activation of both molecules involved in survival signaling and will lead to cancer cell death and sensitivity to chemotherapy. We anticipate that our approach (targeting FAK protein-protein interactions) is amenable to more successful drug discovery and development than the typical method of targeting the kinase activity by targeting ATP binding site of tyrosine kinases. Experience shows that it is especially difficult in the case of FAK, as several large pharmaceutical companies have failed to develop specific inhibitors of FAK that target kinase activity due to cross-reactivity with other essential tyrosine kinases.

The market for novel drug therapy targeting cancers of the breast, colon, pancreas, and thyroid is extensive. According to the American Cancer Society, it is estimated that 425,000 new cases of these cancers will be diagnosed this year in this country alone. Cancer drug therapy is an existing major product line of several pharmaceutical companies, and the development of drugs targeting FAK would be a natural complement to their existing products.

FAK is overexpressed in many cancer types compared to other kinase targets. Compounds that target FAK could be prescribed for many cancer types including breast, colon, pancreas, thyroid, lung, and melanoma.

Several groups are exploring the targeting of FAK as potential cancer therapeutics. The targeting of FAK typically has been focused on the kinase domain of FAK. This approach has proven unsuccessful as disruption of the kinase domain does not specifically interfere with the signaling downstream of FAK and other related tyrosine kinases have been affected by the drugs. Delineated herein is a novel approach that investigates the protein-protein interactions that are very specific for downstream signaling of FAK. Furthermore, targeting different binding partners of FAK might be relevant to different types of tumors.

Our laboratory was the first to clone human Focal Adhesion Kinase in 1993 and demonstrate its upregulation in different human tumors [4, 5]. Based on knowledge of FAK biology in normal and tumor cells, we have identified the protein-protein interactions of FAK as targets for small-molecule-based tumor therapy. Phage display analyses revealed many potential FAK binding partners, some of which we already discovered by different approaches (e.g., p53) [6] and some we characterized based on phage display data (e.g., VEGFR3) [7]. Many of the selected peptides caused loss of viability and apoptosis in cancer but not in normal cells in vitro. These results suggest that it may occur by mimicking binding sites for key partners of FAK. We are focusing on three key structural interactions of FAK and specific binding sites. The advantage of our approach is twofold: we have well-defined data that targeting FAK interactions is important for cell survival, and we have used atomic resolution structural data of specific binding sites to identify small molecule lead compounds [8-10]. We are utilizing these data for structural analyses of FAK binding to these small molecules.

We have identified a series of small molecules that we have evaluated for inhibition of FAK function, followed by application of our extensive experience in FAK biology and our already evaluated model systems to perform multiple cell-based assays (viability, proliferation, motility and invasion, cell cycle and apoptosis) for the analysis of biological activity of the lead compounds. We examined cancer cell lines (e.g., breast, colon, pancreatic, lung, or melanoma human, glioblastoma) with these selected FAK inhibitors.

SUMMARY OF THE INVENTION

In one aspect, the invention provides a method of treating a subject suffering from or susceptible to a cell proliferative disorder comprising administering to subject in need thereof a therapeutically effective amount of a compound capable of modulating FAK protein-protein binding interactions. In one embodiment, the compound is capable of binding to or interacting with a binding pocket that affects FAK binding with vascular endothelial growth receptor 3 VEGFR-3. The compounds of the formulae herein may be used to modulate (e.g., inhibit) the FAK-VEGFR-3 binding interaction. In aspects the compounds bind with the FAT domain of FAK.

In one aspect, the invention provides a method of treating a subject suffering from or susceptible to a cell proliferative disorder. The method includes administering to a subject in need thereof a therapeutically effective amount of a FAK binding inhibitor compound delineated herein.

In another aspect, the invention provides a method of treating a subject suffering from or susceptible to a cell proliferative disorder. The method includes administering to a subject in need thereof a therapeutically effective amount of a compound capable of modulating FAK protein-protein binding interactions by directly modulating the FAK binding partner's binding ability.

In another embodiment, the invention provides a method of treating a subject suffering from or susceptible to a cell proliferative disorder. The method includes administering to a subject identified as in need thereof a therapeutically effective amount of a FAK inhibitor compound or a FAK binding partner inhibitor compound.

In another aspect, the invention provides a method of treating a subject suffering from or susceptible to a cell proliferative disorder, including cancer. The method includes administering to a subject in need thereof a therapeutically effective amount of a compound capable of binding to a the focal adhesion targeting (FAT) domain of FAK or a FAK protein binding partner.

In another aspect, the invention provides a method of treating a subject suffering from or susceptible to cancer, comprising administering to the subject an effective amount of a compound capable of disrupting FAK binding (including with FAK-binding partners), such that the subject is treated.

In another aspect, the invention provides a method of treating a subject suffering from or susceptible to a disorder comprising administering to subject in need thereof a therapeutically effective amount of a compound capable of modulating proliferation, wherein the compound stimulates proliferation. In other aspects, the method comprises stimulating FAK protein-protein binding interactions.

Yet another aspect of the invention is a method for identifying a compound that inhibits cell proliferation. The method includes contacting a focal adhesion targeting domain (FAT) complex with a test compound, and evaluating the ability of the test compound to modulate (e.g., inhibit), the FAT domain of FAK, inhibit cell proliferation, induce apoptosis, or modulate FAK binding with a FAK protein binding partner.

In another aspect, the invention provides a packaged composition including a therapeutically effective amount of a FAK inhibitor or FAK protein-protein binding interaction inhibitor compound and a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In one aspect, the invention provides a kit for treating a cell proliferative disorder in a subject is provided and includes a compound herein, a pharmaceutically acceptable esters, salts, and prodrugs thereof, and instructions for use. In further aspects, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In certain embodiments, the invention provides: a kit for treating a cell proliferative disorder in a subject, the kit comprising a compound capable of modulating (e.g., inhibiting) FAK activity or FAK protein-protein binding interactions.

The invention also provides a pharmaceutical compositions of the compounds described herein, comprising a compound capable of modulating the activity of the FAT domain of FAK or modulate FAK binding with a FAK protein binding partner, or a pharmaceutically acceptable ester, salt, or prodrug thereof, together with a pharmaceutically acceptable carrier.

The invention provides for A compound of formula I:

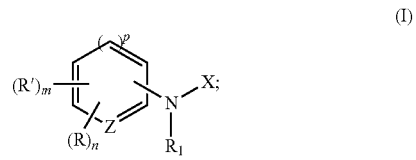

(I)

or a pharmaceutically acceptable salt, ester or prodrug thereof, wherein, Z is N or $CR_A$; X is $—(CH_2)^r—NR_AR_B$; or H; $R_1$ is H, $C_3$-$C_{15}$ alkyl, $C_3$-$C_{15}$ alkenyl, $C_3$-$C_{15}$ alkynyl, or aralkyl, each of which is optionally substituted; wherein X and $R_1$ are not both H; each R is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$; each of which is optionally substituted; each R' is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$; each of which is optionally substituted; or any two of R or R', together with the atoms to which each is attached, may form a fused cycloalkyl, aryl, heterocycloalkyl, or heteroaryl ring, each of which is optionally substituted; $R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; n is 0, 1, or 2; m is 0, 1, or 2; p is 0 or 1; and r is 1, 2, 3, or 4; with the proviso that the compound does not include the following compounds:

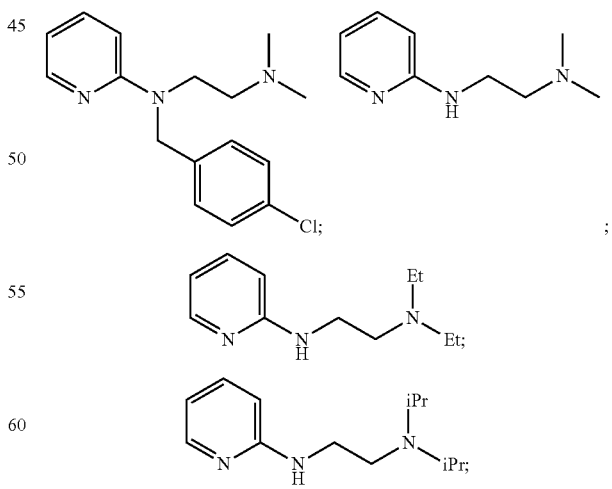

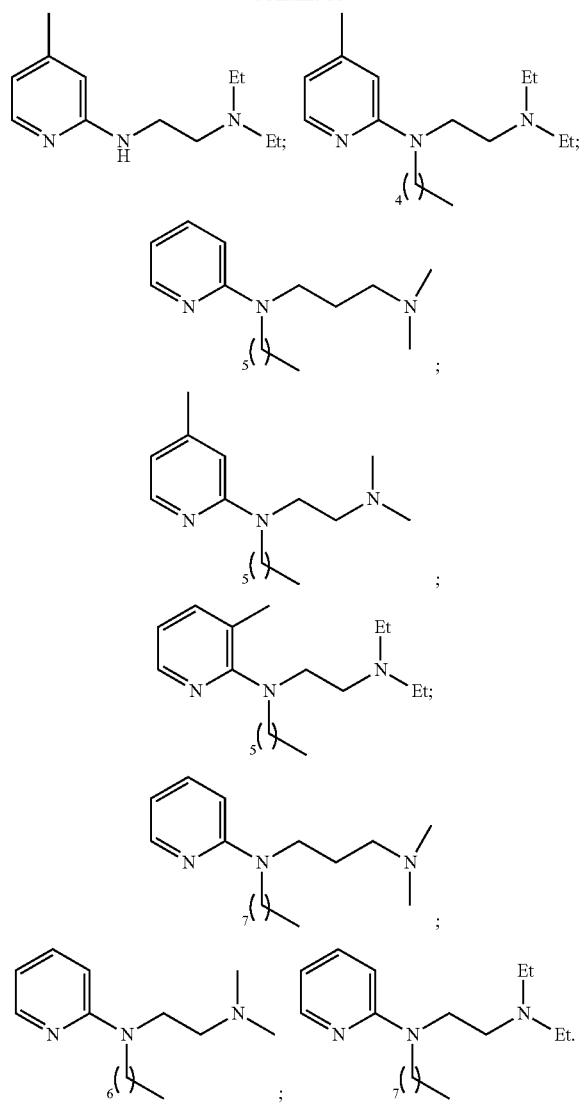

In one embodiment, Z is N.

In another embodiment, Z is CH.

In another embodiment, each R is independently hydrogen, halogen, alkyl, aryl, heterocyclic, or heteroaryl; each of which is optionally substituted.

In another embodiment, each R' is independently hydrogen, halogen, alkyl, aryl, heterocyclic, or heteroaryl; each of which is optionally substituted.

In another embodiment, any two of R or R', together with the atoms to which each is attached, form a fused aryl or heteroaryl ring, each of which is optionally substituted.

In another the fused ring is phenyl, napthyl, anthracenyl, pyridinyl, pyrimidinyl, pyrazinyl, pyridizinyl, triazinyl, furanyl, thienyl, pyrrolyl, pyrazolyl, or imidazolyl; each of which is optionally substituted.

In another embodiment, Z is ortho to —N(X)(R$_1$).

In another embodiment, Z is meta to —N(X)(R$_1$).

In another embodiment, Z is para to —N(X)(R$_1$).

In another embodiment, the compound is of formula II:

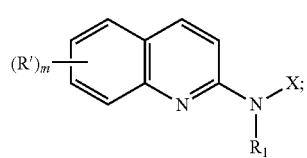

(II)

or a pharmaceutically acceptable salt, ester or prodrug thereof, wherein, X is —(CH$_2$)$_r$—NR$_A$R$_B$; or H; R$_1$ is H, C$_3$-C$_{15}$ alkyl, or aralkyl, each of which is optionally substituted; each R' is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$; each of which is optionally substituted; R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; m is 0, 1, or 2; and r is 1, 2, 3, or 4.

In another embodiment, X is —(CH$_2$)$_r$—NR$_A$R$_B$; and r is 2 or 3.

In another embodiment, R$_A$ is optionally substituted alkyl and R$_B$ is optionally substituted alkyl.

In another embodiment, X is H.

In another embodiment, R$_1$ is benzyl, optionally substituted with 1-4 substituents, each selected from halo, haloalkyl, —OR$_A$, —SR$_A$; wherein each R$_A$ is independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In another embodiment R$_1$ is propyl, hexyl, heptyl, octyl, decyl, or dodecyl.

In another embodiment, R$_1$ is H.

In another the compound is of formula III:

(III)

or a pharmaceutically acceptable salt, ester or prodrug thereof, wherein, X is —(CH$_2$)$_r$—NR$_A$R$_B$; or H; R$_1$ is H, C$_3$-C$_{15}$ alkyl, or aralkyl, each of which is optionally substituted; each R' is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$; each of which is optionally substituted; R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; m is 0, 1, or 2; and r is 1, 2, 3, or 4.

In another embodiment, X is —(CH$_2$)$_r$—NR$_A$R$_B$; and r is 2 or 3.

In another embodiment, R$_A$ is optionally substituted alkyl and R$_B$ is optionally substituted alkyl.

In another embodiment, X is H.

In another embodiment, R$_1$ is benzyl, optionally substituted with 1-4 substituents, each selected from halo, haloalkyl, —OR$_A$, —SR$_A$;

In another embodiment, each R$_A$ is independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In another embodiment, R$_1$ is propyl, hexyl, heptyl, octyl, decyl, or dodecyl.

In another embodiment, R$_1$ is H.

In another embodiment, the compound is of formula IV:

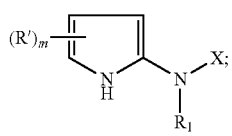

(IV)

or a pharmaceutically acceptable salt, ester or prodrug thereof,
wherein, X is —(CH$_2$)$_r$—NR$_A$R$_B$; or H; R$_1$ is H, C$_3$-C$_{15}$ alkyl, or aralkyl, each of which is optionally substituted; each R' is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$) S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$; each of which is optionally substituted; R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; m is 0, 1, or 2; and r is 1, 2, 3, or 4.

In another embodiment, X is —(CH$_2$)$_r$—NR$_A$R$_B$; and r is 2 or 3.

In another embodiment, R$_A$ is optionally substituted alkyl and R$_B$ is optionally substituted alkyl.

In another embodiment, X is H.

In another embodiment, R$_1$ is benzyl, optionally substituted with 1-4 substituents, each selected from halo, haloalkyl, —OR$_A$, —SR$_A$; wherein each R$_A$ is independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In another embodiment, R$_1$ is propyl, hexyl, heptyl, octyl, decyl, or dodecyl.

In another embodiment, R$_1$ is H.

In another embodiment, the compound of formula VI:

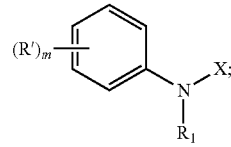

(VI)

or a pharmaceutically acceptable salt, ester or prodrug thereof, wherein, X is —(CH$_2$)$_r$—NR$_A$R$_B$; or H; R$_1$ is H, C$_3$-C$_{15}$ alkyl, or aralkyl, each of which is optionally substituted; each R' is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$) NR$_A$R$_B$, —NR$_A$R$_B$, —C(O)OR$_A$, —C(O)R$_A$, —C(O) NR$_A$R$_B$, or —N(R$_A$)C(O)R$_B$; each of which is optionally substituted; R$_A$ and R$_B$ are each independently selected at each occurrence from the following: optionally substituted alkyl, optionally substituted alkenyl or optionally substituted alkynyl, each containing 0, 1, 2, or 3 heteroatoms selected In another embodiment, the compound is of formula V:

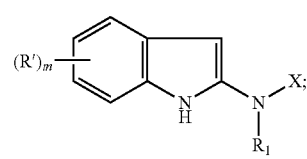

(V)

or a pharmaceutically acceptable salt, ester or prodrug thereof, wherein, X is —(CH$_2$)$_r$—NR$_A$R$_B$; or H; R$_1$ is H, C$_3$-C$_{15}$ alkyl, or aralkyl, each of which is optionally substituted; each R' is independently hydrogen, halogen, alkyl, aryl, heterocyclic, heteroaryl, silyl, fatty acid ester, acyloxy, aralkyl, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$) NR$_A$R$_B$, —NR$_A$R$_B$, —C(O)OR$_A$, —C(O)R$_A$, —C(O) NR$_A$R$_B$, or —N(R$_A$)C(O)R$_B$; each of which is optionally substituted; R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; m is 0, 1, or 2; and r is 1, 2, 3, or 4.

In another embodiment, X is —(CH$_2$)$_r$—NR$_A$R$_B$; and r is 2 or 3.

In another embodiment, R$_A$ is optionally substituted alkyl and R$_B$ is optionally substituted alkyl.

In another embodiment, X is H.

In another embodiment, R$_1$ is benzyl, optionally substituted with 1-4 substituents, each selected from halo, haloalkyl, —OR$_A$, —SR$_A$; wherein each R$_A$ is independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In another embodiment, R$_1$ is propyl, hexyl, heptyl, octyl, decyl, or dodecyl.

In another embodiment, R$_1$ is H.

In another embodiment, the compound is selected from the following:

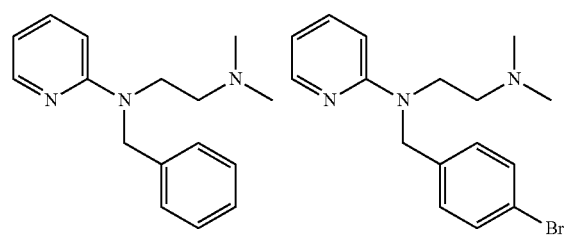

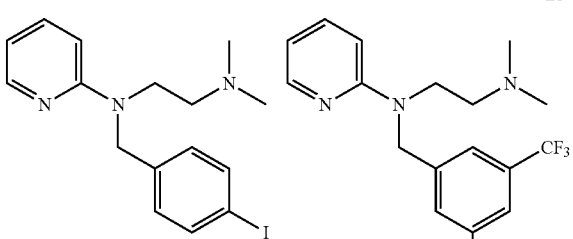

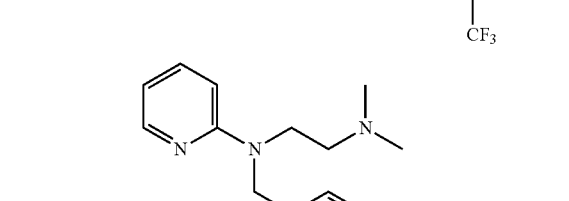

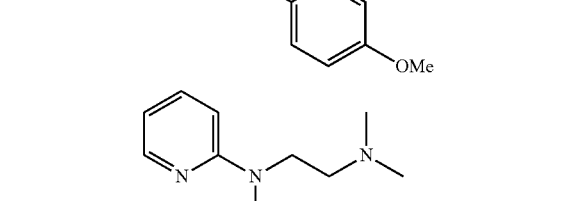

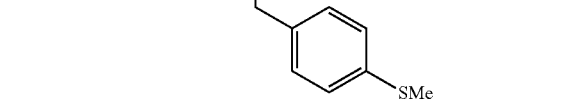

-continued

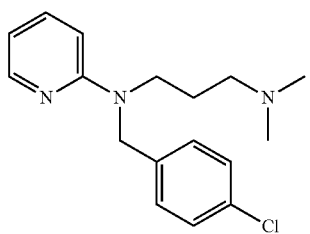

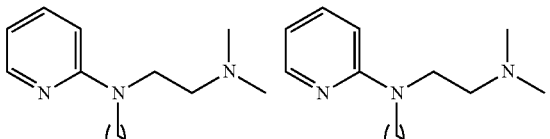

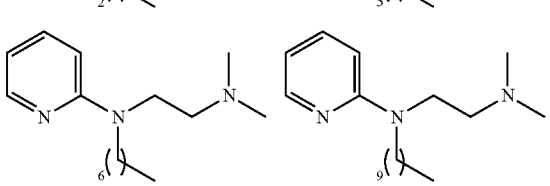

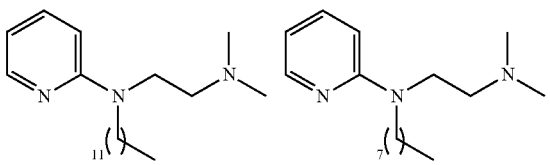

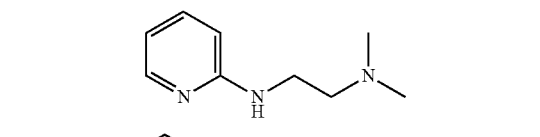

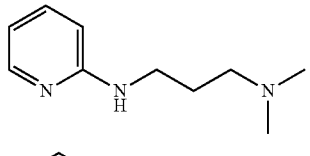

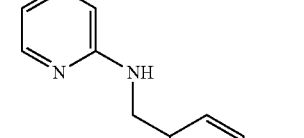

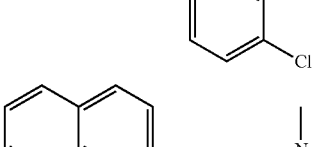

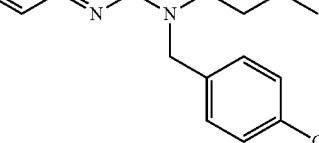

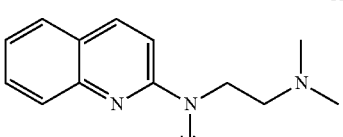

In another embodiment, X is —(CH$_2$)$_r$—NR$_A$R$_B$; and r is 2.

In another embodiment m is 0.

In another embodiment, R$_1$ is propyl, hexyl, heptyl, octyl, decyl, or dodecyl.

In another embodiment, X is —(CH$_2$)$_r$—NR$_A$R$_B$; R$_A$ and R$_B$ are each independently alkyl; r is 2; R$_1$ is propyl, hexyl, heptyl, octyl, decyl, or dodecyl; and m is 0.

In another embodiment, X is —(CH$_2$)$_r$—NR$_A$R$_B$; and r is 2.

In another embodiment, m is 0.

In another embodiment, R$_1$ is aralkyl optionally substituted with 1, 2 or 3 substituents independently selected from hydroxy, halogen, cyano, nitro, C$_1$-C$_8$alkyl, C$_1$-C$_8$alkoxy, C$_8$alkylthio, amino, mono- or di-(C1-C$_8$alkyl)amino.

In another embodiment, R$_1$ is aralkyl optionally substituted with 1, 2 or 3 substituents independently selected from hydroxy, halogen, C$_1$-C$_8$alkyl, or C$_1$-C$_8$alkoxy.

In another embodiment, X is —(CH$_2$)$_r$—NR$_A$R$_B$; R$_A$ and R$_B$ are each independently alkyl; r is 2; R$_1$ is aralkyl optionally substituted with 1, 2 or 3 substituents independently selected from hydroxy, halogen, cyano, nitro, C$_1$-C$_8$alkyl, C$_1$-C$_8$alkoxy, C$_1$-C$_8$alkylthio, amino, mono- or di-(C1-C$_8$alkyl)amino; and m is 0.

The invention also provides for a pharmaceutical composition comprising any one of the compounds of the invention, or a pharmaceutically acceptable ester, salt, or prodrug thereof, together with a pharmaceutically acceptable carrier.

The invention also provides for a method of inducing apoptosis in a cancer cell in a subject comprising administering to the subject identified as in need thereof any one of the compounds of the invention capable of inhibiting the binding interaction of focal adhesion kinase (FAK) with VEGFR-3.

In one embodiment, administering is via an oral route.

In another embodiment, the compound inhibits FAK binding at the focal adhesion targeting sequence (FAT) domain.

In another embodiment, the cancer is breast, brain, colon, pancreatic, thyroid, lung, melanoma, gastric, neuroblastoma, leukemia, or lymphoma.

A method of inhibiting a FAK protein-protein binding interaction in a subject identified as in need of such treatment, comprising administering any one of the compounds of the invention identified as capable of inhibiting the FAK protein-VEGFR3 interaction.

The invention also provides for a method of treating cancer in a subject comprising administering to the subject identified as in need thereof any one of the compounds of the invention capable of inhibiting the binding interaction of focal adhesion kinase (FAK) with VEGFR3.

In one embodiment, the binding interaction with VEGFR3 and FAK results in modulation of apoptosis or cellular proliferation of cancer cells.

In another embodiment, the cancer is breast, brain, colon, pancreatic, thyroid, lung, melanoma, gastric, neuroblastoma, leukemia, or lymphoma.

In another embodiment, administering is via an oral route

In another embodiment, the method further comprising an additional therapeutic agent.

In another embodiment, the additional therapeutic agent is doxorubicin, cisplatin, taxol, 5-fluorouracil, etoposid, temozolomide or gemcitabine.

BRIEF DESCRIPTION OF THE DRAWINGS

The present invention is further described below with reference to the following non-limiting examples and with reference to the following figures, in which:

FIG. 6. shows the efficacy of compounds 9A, 9B, and C10 on tumor growth in xenografted nude mice.

DETAILED DESCRIPTION OF THE INVENTION

Figure 1:
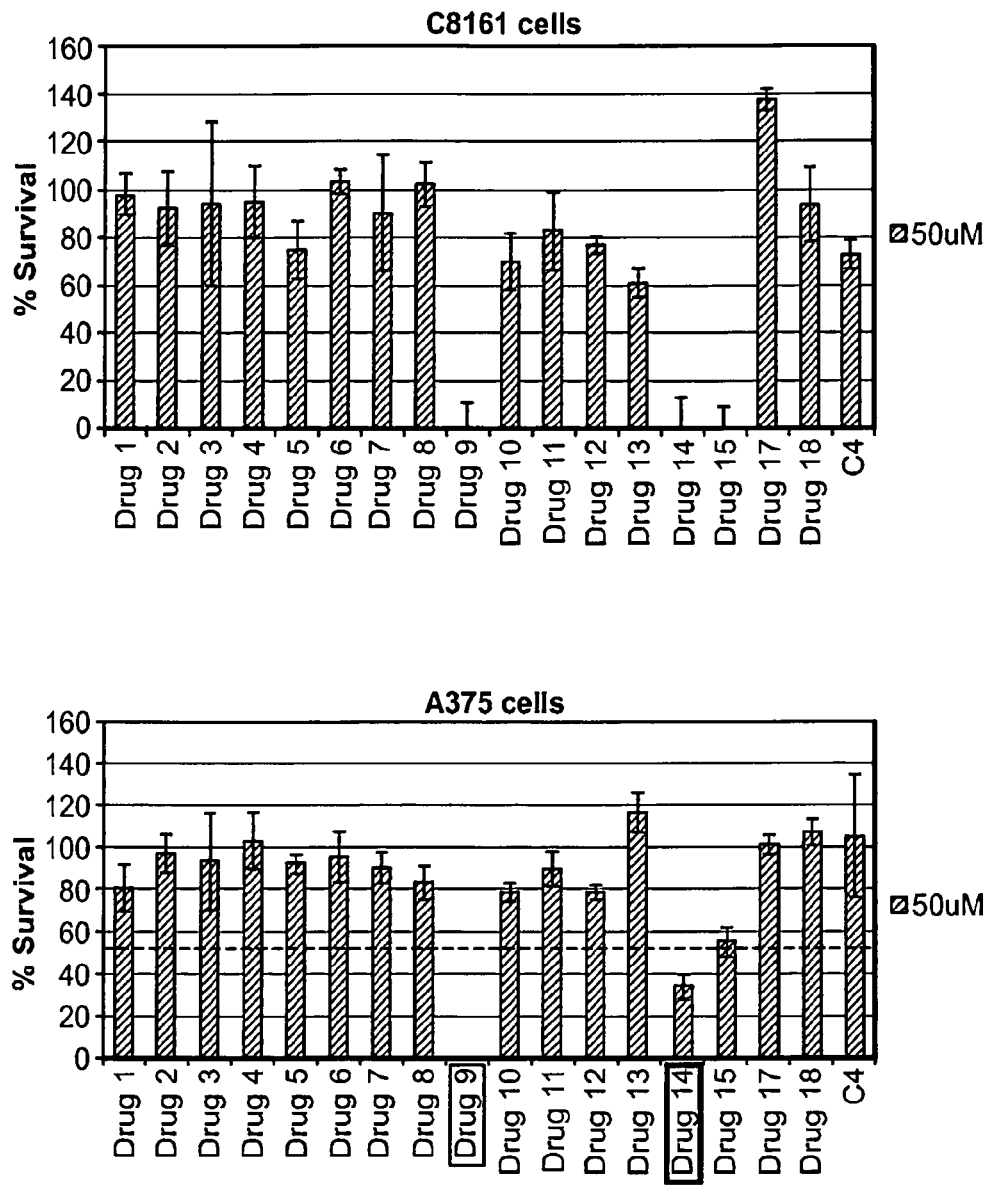
FIG. 1. depicts the effect of compounds of the invention on melanoma cells

The present inventors have now discovered a therapeutic strategy that addresses inhibition of FAK by targeting FAK protein-protein binding interactions with FAK binding partners. Such interactions are relevant for modulation of apoptosis and cell proliferation, particularly in certain cancer types where FAK mechanisms play a significant role.

The present invention relates, at least in part, to the discovery that the FAK protein-protein interactions are useful as targets (e.g., selective) for tumor therapy. Phage display analyses reveal potential FAK binding partners. Disruption of these binding interactions cause loss of viability and apoptosis in cancer but not in normal cells in vitro.

1. DEFINITIONS

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The terms "halogen", "halo" or "hal" designate —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors or cancers (e.g., lung (small cell and non-small cell), thyroid, prostate, pancreatic, breast or colon), sarcoma or melanoma.

The language "a FAK protein-protein binding partner" refers to a protein (including those delineated herein) that bind with FAK (e.g., full length, N-terminus, C-terminus, carboxy terminus, kinase domain, FERM domain, FAT domain).

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-C8alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of modulating FAK or FAK protein-protein interaction partner binding" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention of the invention, such as human and non-human animals. Preferred humans include human patients suffering from or prone to suffering from a cell proliferative disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. COMPOUNDS OF THE INVENTION

In one aspect, the invention provides compounds capable of modulating (e.g., inhibiting or stimulating) (directly or indirectly) FAK binding activity. In another aspect is a combination of a compound capable of modulating (e.g., inhibiting or stimulating) (directly or indirectly) FAK binding activity and an additional therapeutic agent, e.g., a chemotherapeutic agent.

In one embodiment, the invention provides a compound capable of modulating FAK protein-protein binding; and pharmaceutically acceptable esters, salts, and prodrugs thereof having the structure of:

A compound of formula I:

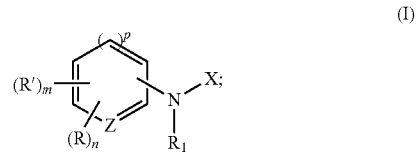

or a pharmaceutically acceptable salt, ester or prodrug thereof,
wherein,
Z is N or $CR_A$;
X is —$(CH_2)_r$—$NR_AR_B$; or H;
$R_1$ is H, $C_3$-$C_{15}$ alkyl, $C_3$-$C_{15}$ alkenyl, $C_3$-$C_{15}$ alkynyl, or aralkyl, each of which is optionally substituted; wherein X and $R_1$ are not both H;

each R is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)$ $S(O_2)$ $NR_AR_B$, —$NR_AR_B$, —C(O)$OR_A$, —C(O)$R_A$, —C(O) $NR_AR_B$, or —$N(R_A)C(O)R_B$; each of which is optionally substituted;

each R' is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)$ $S(O_2)$ $NR_AR_B$, —$NR_AR_B$, —C(O)$OR_A$, —C(O)$R_A$, —C(O) $NR_AR_B$, or —$N(R_A)C(O)R_B$; each of which is optionally substituted;

or any two of R or R', together with the atoms to which each is attached, may form a fused cycloalkyl, aryl, heterocycloalkyl, or heteroaryl ring, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

n is 0, 1, or 2;
m is 0, 1, or 2;
p is 0 or 1; and
r is 1, 2, 3, or 4;

with the proviso that the compound does not include the following compounds:

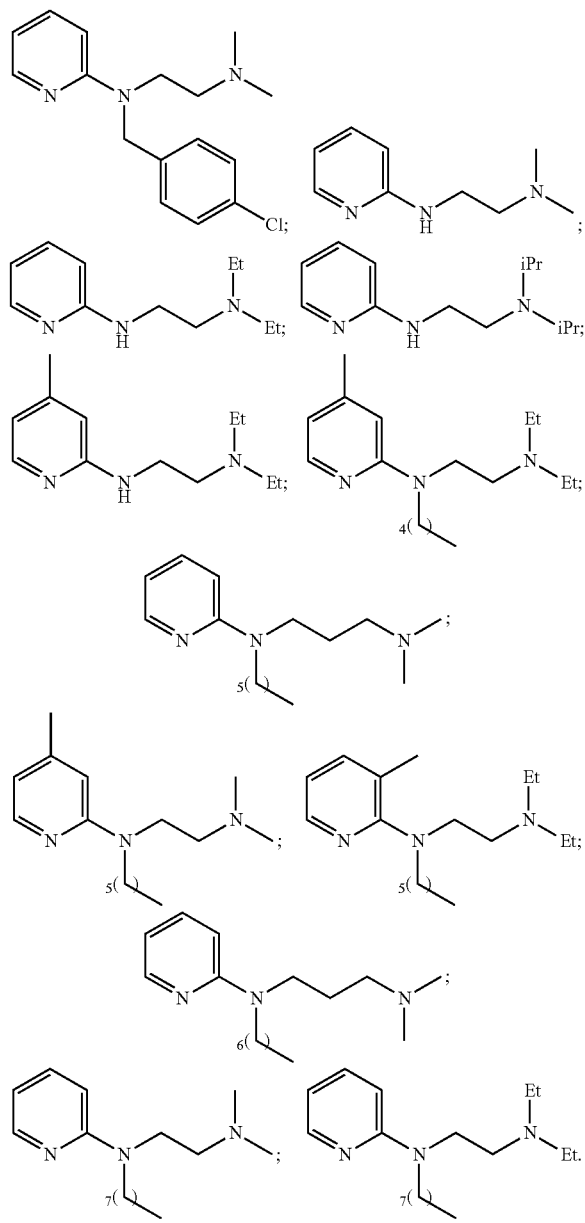

In other aspects, the compounds are those of the formulae herein:
wherein Z is N;
wherein Z is CH;
wherein each R is independently hydrogen, halogen, alkyl, aryl, heterocyclic, or heteroaryl; each of which is optionally substituted;
wherein each R' is independently hydrogen, halogen, alkyl, aryl, heterocyclic, or heteroaryl; each of which is optionally substituted;
wherein any two of R or R', together with the atoms to which each is attached, form a fused aryl or heteroaryl ring, each of which is optionally substituted;
wherein the fused ring is phenyl, napthyl, anthracenyl, pyridinyl, pyrimidinyl, pyrazinyl, pyridizinyl, triazinyl, furanyl, thienyl, pyrrolyl, pyrazolyl, or imidazolyl; each of which is optionally substituted;
wherein Z is ortho to —N(X)($R_1$);
wherein Z is meta to —N(X)($R_1$); wherein Z is para to —N(X)($R_1$);

In another aspect, the compound is of the formulae above, wherein:
compound is of formula II:

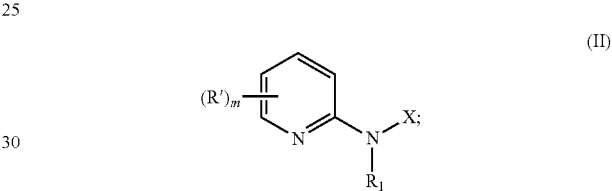

(II)

or a pharmaceutically acceptable salt, ester or prodrug thereof,
wherein,
X is —$(CH_2)_r$—$NR_AR_B$; or H;
$R_1$ is H, $C_3$-$C_{15}$ alkyl, or aralkyl, each of which is optionally substituted;
each R' is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —C(O)$OR_A$, —C(O)$R_A$, —C(O)$NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

m is 0, 1, or 2; and
r is 1, 2, 3, or 4.

In other aspects, the compounds are those of the formulae herein:
wherein X is —$(CH_2)_r$—$NR_AR_B$; and r is 2 or 3;
wherein $R_A$ is optionally substituted alkyl and $R_B$ is optionally substituted alkyl;
wherein X is H;
wherein $R_1$ is benzyl, optionally substituted with 1-4 substituents, each selected from halo, haloalkyl, —$OR_A$, —$SR_A$;
wherein each $R_A$ is independently selected at each occurrence from the following: optionally substituted alkyl, optionally substituted alkenyl or optionally substituted alkynyl, each containing 0, 1, 2, or 3 heteroatoms selected from O, S, or N;

optionally substituted aryl; optionally substituted heteroaryl; optionally substituted heterocyclic; optionally substituted carbocyclic; or hydrogen;

wherein $R_1$ is propyl, hexyl, heptyl, octyl, decyl, or dodecyl;

wherein $R_1$ is H.

In another aspect, the compound is of the formulae above, wherein:

the compound is of formula III:

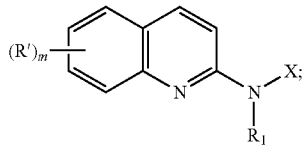

(III)

or a pharmaceutically acceptable salt, ester or prodrug thereof,
wherein,

X is —$(CH_2)_r$—$NR_AR_B$; or H;

$R_1$ is H, $C_3$-$C_{15}$ alkyl, or aralkyl, each of which is optionally substituted;

each R' is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)$ $S(O_2)$ $NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

m is 0, 1, or 2; and r is 1, 2, 3, or 4.

In another aspect, the compound is of the formulae above, wherein:

the compound is of formula IV:

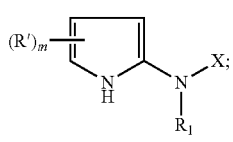

(IV)

or a pharmaceutically acceptable salt, ester or prodrug thereof,
wherein,

X is —$(CH_2)_r$—$NR_AR_B$; or H;

$R_1$ is H, $C_3$-$C_{15}$ alkyl, or aralkyl, each of which is optionally substituted;

each R' is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)$ $S(O_2)$ $NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

m is 0, 1, or 2; and r is 1, 2, 3, or 4.

In another aspect, the compound is of the formulae above, wherein:

the compound is of formula V:

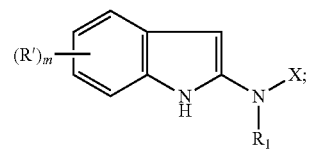

(V)

or a pharmaceutically acceptable salt, ester or prodrug thereof,
wherein,

X is —$(CH_2)_r$—$NR_AR_B$; or H;

$R_1$ is H, $C_3$-$C_{15}$ alkyl, or aralkyl, each of which is optionally substituted;

each R' is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)$ $S(O_2)$ $NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

m is 0, 1, or 2; and r is 1, 2, 3, or 4.

In another aspect, the compound is of the formulae above, wherein:

the compound is of formula VI:

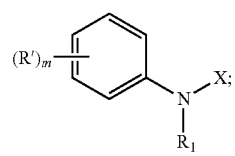

(VI)

or a pharmaceutically acceptable salt, ester or prodrug thereof,
wherein,

X is —$(CH_2)_r$—$NR_AR_B$; or H;

$R_1$ is H, $C_3$-$C_{15}$ alkyl, or aralkyl, each of which is optionally substituted;

each R' is independently hydrogen, halogen, alkyl, aryl, heterocyclic, heteroaryl, silyl, fatty acid ester, acyloxy, aralkyl, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)$ $S(O_2)$ $NR_AR_B$, —$NR_AR_B$, —$C(O)OR_A$, —$C(O)R_A$, —$C(O)NR_AR_B$, or —$N(R_A)C(O)R_B$; each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

m is 0, 1, or 2; and r is 1, 2, 3, or 4.

NOMENCLATURE

Certain compounds of this invention have been given numerical designations, e.g. Drug 1, 2, 3, 4, 5, 6, 7, 8, 9, 9A, 9B, 10, 11, 12, 13, 14, 15, 17 and 18. These are alternatively and respectively referred to as C1, C2, C3, C4, C5, C6, C7, C8, C9, C9A, C9B, C10, C11, C12, C13, C14, C15, C17 and C18. The chemical structures of these compounds are shown in the table in this specification. The compounds of this invention have been studied alongside another molecule, chloropyramine, which is sometimes given the designation "C4" in figures and tables.

Certain preferred compounds include compounds specifically delineated herein selected from the following:

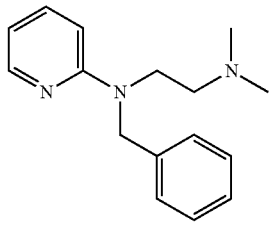

C2

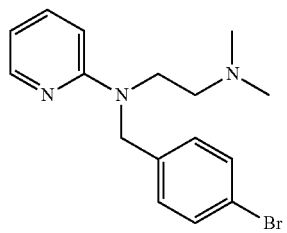

C3

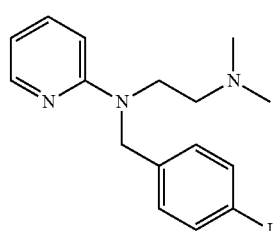

-continued

C4

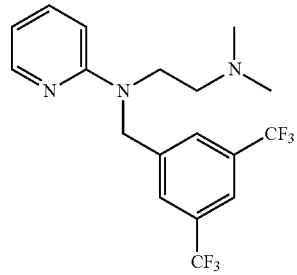

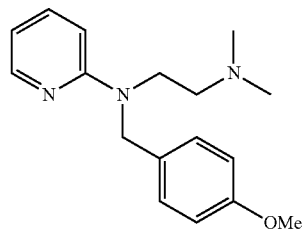

C12

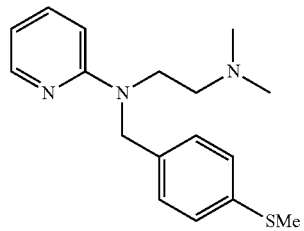

C7

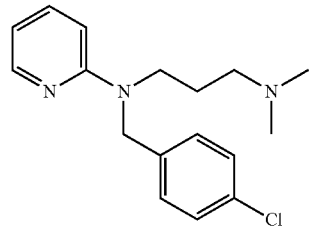

C8

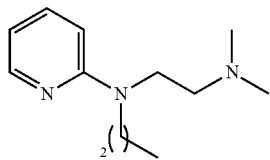

C6

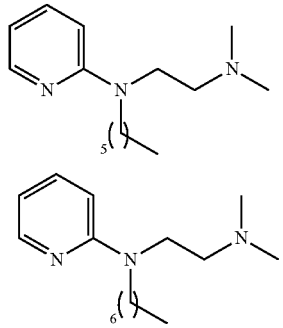

-continued

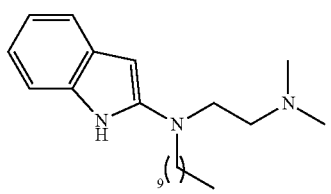

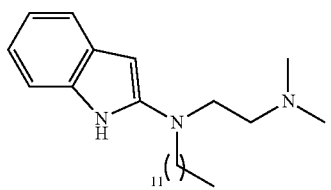

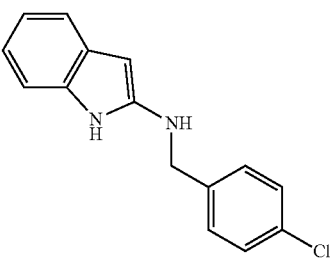

C15

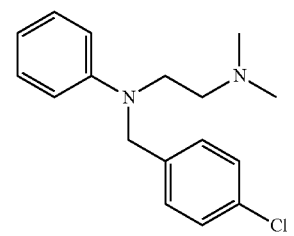

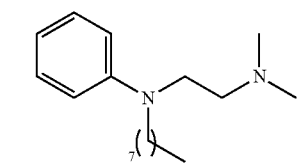

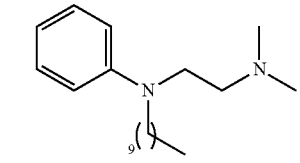

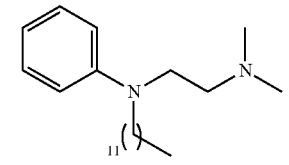

C14

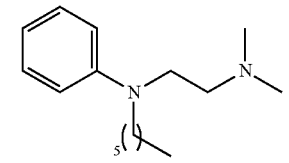

C13

-continued

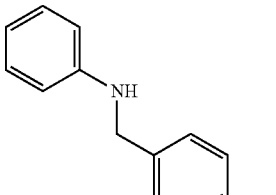

C16

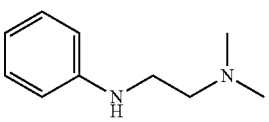

The invention also relates to the pharmaceutically acceptable salts and esters of the above-mentioned compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention.

In embodiments, the invention provides for the intermediate compounds of the formulae delineated herein and methods of converting such compounds to compounds of the formulae herein (e.g., in Schemes 1 and 2, G1 to G2; G3 to G4; G4 to G5; G3 to G5) comprising reacting a compound herein with one or more reagents in one or more chemical transformations (including those provided herein) to thereby provide the compound of any of the formulae herein or an intermediate compound thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula (e.g., in Schemes 1 and 2, G1 to G2; G3 to G4; G4 to G5; G3 to G5). The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds which associate with or bind to a FAK binding pocket or a FAK protein-protein binding partner binding pocket (including binding sites where FAK binds with the partner or other binding sites in the partner) produced or identified by the methods described herein.

3. USES OF THE COMPOUNDS OF THE INVENTION

In one embodiment, the invention provides methods for treating a subject for a cell proliferative disorder, by administering to the subject an effective amount of a compound capable of disrupting FAK binding with a FAK protein-protein binding partner. A cell proliferative disorder includes cancer. In certain embodiments, the subject is a mammal, e.g., a primate, e.g., a human.

In this embodiment, the compounds of the invention may either directly or indirectly modulate the activity of FAK, FAK binding partner, or specific domains thereof. A cell undergoing uncontrolled proliferation can be contacted with a compound of the invention to inhibit cell proliferation or induce apoptosis. Contacting cells or administering the compounds of the invention to a subject is one method of treating a cell or a subject suffering from or susceptible to unwanted or undesired cell proliferation or a cell proliferative disorder.

In one embodiment, a method of treating a subject suffering from or susceptible to unwanted or undesired cell proliferation or a cell proliferative disorder includes administering to a subject in need thereof a therapeutically effective amount of a compound capable of directly or indirectly modulate the activity of FAK, FAK binding partner, or specific domains thereof, to thereby treat the subject suffering from or susceptible to unwanted or undesired cell proliferation or a cell proliferative disorder. Exemplary compounds include compounds described herein.

Thus, in one embodiment, the invention provides methods for treating a subject for a cell proliferative disorder, by administering to the subject an effective amount of a compound capable of binding to a binding pocket of FAK or a FAK binding partner.

The compounds and compositions herein are useful to treat or prevent FAK-mediated disease, e.g., diseases involving FAK-VEGFR-3 interaction. Examples of such disease include, but are not limited to: breast, colon, pancreatic, thyroid, lung, melanoma, brain cancer, and glioblastoma multiforme.

In certain embodiments, the methods of the invention include administering to a subject a therapeutically effective amount of a compound of the invention in combination with another pharmaceutically active compound. Examples of pharmaceutically active compounds include compounds known to treat cell proliferative disorders, e.g., anticancer agent, antiproliferative agent, chemotherapeutic. Other pharmaceutically active compounds that may be used can be found in *Harrison's Principles of Internal Medicine*, Thirteenth Edition, Eds. T. R. Harrison et al. McGraw-Hill N.Y., N.Y.; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional cancer chemotherapeutics. Conventional treatment regimens for leukemia and for other tumors include radiation, drugs, or a combination of both. In addition to radiation, the following drugs, usually in combinations with each other, are often used to treat acute leukemias: vincristine, prednisone, methotrexate, mercaptopurine, cyclophosphamide, and cytarabine. Other examples include, for example, doxorubicin, cisplatin, taxol, 5-fluorouracil, etoposid, etc., which demonstrate advantages (e.g., chemosensitization of cells) in combination with the compounds described herein. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse. The compounds of the invention can also administered in combination with chemotherapy agents such as doxorubicin or gemcitabine. In particular, the compound C9 is useful in combination with doxorubicin or gemcitabine, or combinations thereof. Thus, compounds of the invention can be used in combination with agents such as temozolomide, taxol, dacarbazine and oxaliplatin.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., those described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

In another aspect, a compound of the invention is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In another aspect, the invention provides methods for inhibiting cell proliferation. In one embodiment, a method of inhibiting cell proliferation (or a cell proliferative disorder) according to the invention includes contacting cells with a compound capable of modulating FAK, FAK binding partner, or specific domains thereof. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a cell proliferative disorder in a subject include administering an effective amount of a compound of the invention (i.e., a compound described herein) to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to a conditions capable of increasing susceptibility to a cell proliferative disorder, e.g., exposure to carcinogens or to ionizing radiation.

In one aspect, a method of monitoring the progress of a subject being treated with a compound herein includes determining the pre-treatment status (e.g., size, growth rate, or invasiveness of a tumor) of the cell proliferative disorder, administering a therapeutically effective amount of a compound herein to the subject, and determining the status (e.g., size, growth rate, or invasiveness of a tumor) of the cell proliferative disorder after an initial period of treatment with the compound, wherein the modulation of the status indicates efficacy of the treatment.

The subject may be at risk of a cell proliferative disorder, may be exhibiting symptoms of a cell proliferative disorder, may be susceptible to a cell proliferative disorder and/or may have been diagnosed with a cell proliferative disorder.

If the modulation of the status indicates that the subject may have a favorable clinical response to the treatment, the subject may be treated with the compound. For example, the subject can be administered therapeutically effective dose or doses of the compound.

In another aspect, methods for evaluating a test compound comprise contacting a FAK, FAK binding partner, or specific domains thereof with a test compound (complex), and evaluating the binding interaction following contact, wherein a change in the stability of the complex relative to a reference value is an indication that the test compound modulates the stability of the complex.

The FAK, FAK binding partner, or specific domains thereof complex may be modeled in silico, or may be a complex within a cell, isolated from a cell, recombinantly expressed, purified or isolated from a cell or recombinant expression system or partially purified or isolated from a cell or recombinant expression system.

Kits of the invention include kits for treating a cell proliferative disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

The present method can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179,109—fetal rat tissue culture), or other mammalian (See e.g. U.S. Pat. No. 5,089,517—fetal mouse tissue culture) or non-mammalian animal models.

Alternatively, the effects of compound of the invention can be characterized in vivo using animals models.

4. PHARMACEUTICAL COMPOSITIONS

The invention also provides a pharmaceutical composition, comprising an effective amount of a compound of the and a pharmaceutically acceptable carrier. In a further embodiment, the effective amount is effective to treat a cell proliferative disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; ($1_3$) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Several of the compounds of this invention may be particularly suited for oral administration. Compounds 9, 9A, 9B and 10 are very effective when administered orally, in contrast to chloropyramine, which is most effective when delivered intraperitoneally. In addition, the effective dose of Compound 9 can be as much as two-, three-, four- or five-times lower than the effective dose for chloropyramine (C4), when it is delivered either orally or intraperitoneally.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

EXAMPLES

The invention is further illustrated by the following examples which are intended to illustrate but not limit the scope of the invention. Definitions of variables in the structures in schemes herein are commensurate with those of corresponding positions in the formulae delineated herein.

Example 1

General Synthesis

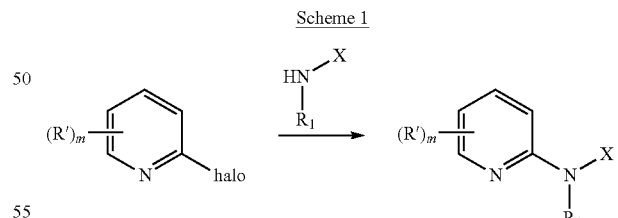

Scheme 1

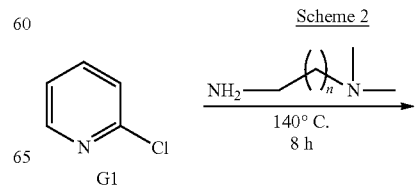

Scheme 2

-continued

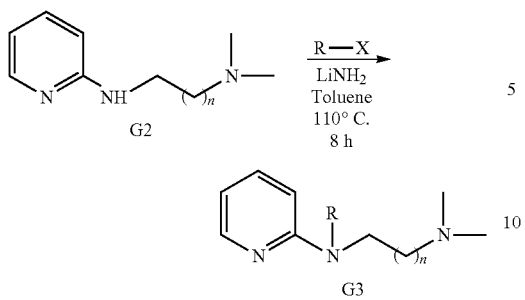

Example 2

Synthesis of Compound 2-3

In a dry 25 ml sealed tube, 2-chloropyridine 2-1 (10 eq, 1.13 g) and N,N-dimethylethylenediamine 2-2 (11 eq, 1.20 g) were taken and heated the entire mixture to 140° C. over a period of 12 h with constant stirring. Then, the reaction mixture was cooled down to room temperature and the resulting crude was purified on a silica gel column by eluting (5% MeOH-DCM) as a solvent mixture to afford the desired derivative 2-3 (0.910 g) in 55% yield.

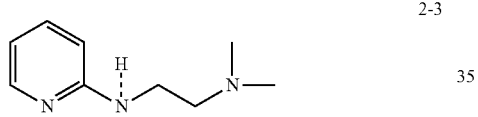

2-3

$^1$H NMR 400 MHz (CDCl$_3$) δ: 8.08 (dd, J=4.8 Hz, J=0.8 Hz, 1H); 7.38 (dt, J=7.2 Hz, J=2 Hz, 1H); 6.54 (dt, J=5.6 Hz, J=0.8 Hz, 1H); 6.40 (d, J=8.4 Hz, 1H); 5.04 (brS, NH, 1H); 3.36 (q, J=5.6 Hz, 2H); 2.55 (t, J=6.0 Hz 2H); 2.27 (s, 6H). Mass (ESI): ink 166 (M+1).

Example 3

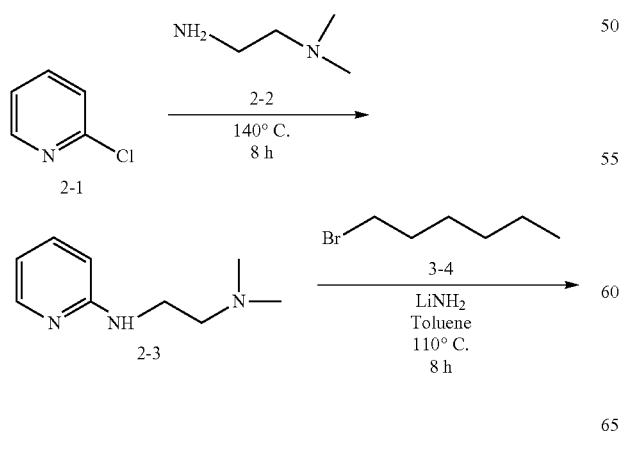

-continued

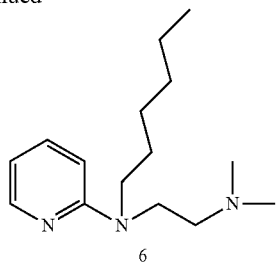

6

Synthesis of Compound 6

The compound 2-3 (1 eq) and LiNH$_2$ (1 eq) were taken in a dry RB flask and was added dry Tolunen (10 mL) as a solvent. After stirring for 5 min under Ar atm, the hexylbromide 3-4 (1 eq) was added drop by drop via syringe. The entire mixture was refluxed at 110° C. for 8 h. The TLC indicated the formation of the new product spot. The reaction mixture was filtered and the filtrate was evaporated under reduced pressure. The crude obtained was purified on a silica gel column. Elution of 1% MeOH-DCM solvent mixture delivered the expected alkylated derivative 6 in 62% yield.

Compound 6:

$^1$H NMR 400 MHz (CD$_3$OD) δ: 7.96 (d, J=4.0 Hz, 1H), 7.31 (t, J=6.8 Hz, 1H); 6.68 (d, J=7.2 Hz, 1H); 6.52 (t, J=6.8 Hz, 1H); 3.94 (m, 2H); 3.76 (m, 2H); 3.55 (m, 2H); 3.37 (s, 6H); 1.67 (m, 2H); 1.21-1.30 (m, 6H), 0.81 (t, J=5.6 Hz, 3H). Mass (ESI): m/e 266 (M+1).

Example 4

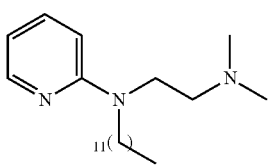

C9

Synthesis of Compound 9

Compound 9 (C9) is made essentially according to the protocol of Example 3 using dodecyl bromide in place of bromide 3-4.

Example 5

Synthesis of C-10

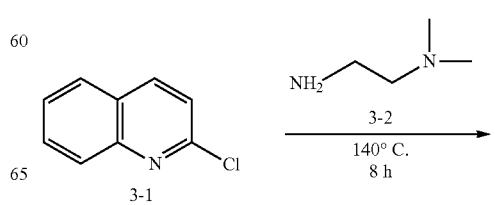

-continued

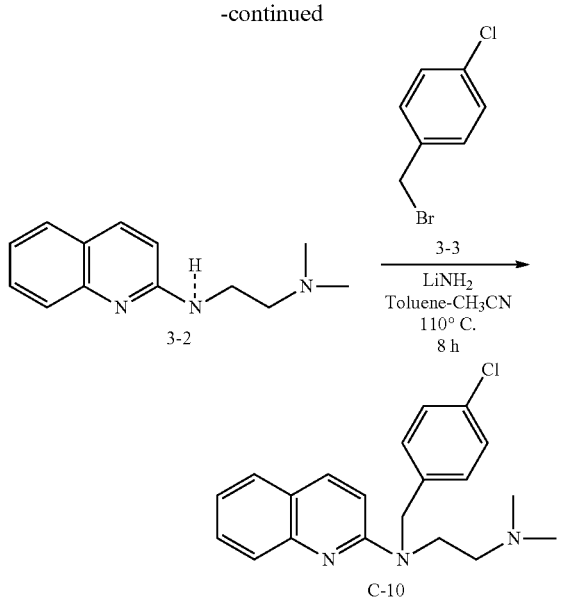

Synthesis of Compound 3-2

2-chloroquinoline 3-1 (10 eq, 1.63 g) and N,N-dimethylethylenediamine 3-2 (11 eq, 1.20 g) were heated to 140° C. over a period of 12 h with constant stirring in a dry 25 ml sealed tube. The reaction mixture was cooled down to room temperature and the resulting crude mixture was purified on a silica gel column by elution (10% MeOH-DCM) as a solvent mixture to produce the desired derivative 3-2 (0.951 g) in a 41% yield $^1$H NMR 400 MHz (CD$_3$OD) δ: 7.82 (d, J=8.8 Hz, 1H); 7.58 (t, J=8.4 Hz, 2H), 7.47 (t, J=8.0 Hz, 1H); 7.16 (t, J=8.0 Hz, 1H); 6.72 (d, J=8.8 Hz, 1H); 3.60 (t, J=6.8 Hz, 2H); 2.64 (t, J=6.8 Hz 2H); 2.34 (s, 6H). Mass (ESI): m/e 232 (M+1).

Synthesis of Compound C-10

The compound 3-2 (1 eq) and LiNH$_2$ (1 eq) were combined in a dry RB flask to which was added dry Toluene-CH$_3$CN (7 mL:3 mL) as a solvent. After stirring for 5 min under Ar atm, the 4-Chlorobenzylbromide 3-3 (1 eq) was added dropwise via syringe. The entire mixture was refluxed at 110° C. for 8 h. The TLC indicated the formation of the new product spot. The reaction mixture was filtered and the filtrate was evaporated under reduced pressure. The crude mixture obtained was purified on a silica gel column. Elution of 20% MeOH-DCM solvent mixture delivered the expected alkylated derivative C-10 in 68% yield.

$^1$H NMR 400 MHz (CD$_3$OD) δ: 7.89 (d, J=8.8 Hz, 1H), 7.61-7.64 (m, 4H), 7.48-7.54 (m, 3H); 7.23 (t, J=6.8 Hz, 1H); 6.80 (d, J=8.8 Hz, 1H); 4.69 (s, 2H), 4.10 (t, J=6.8 Hz, 1H); 3.67 (t, J=6.8 Hz, 1H); 3.19 (s, 6H). Mass (ESI): m/e 340 (M+1).

Methods
Cells and Cell Culture.

Human pancreatic cancer cell lines cells lines (ATCC) were maintained as follows: in Dulbecco's modified Eagle's medium with 4 mM L-glutamine, 0.1 mM nonessential amino acids, 1 µg/mL penicillin and 1 µg/mL streptomycin, and 10% fetal bovine serum (FBS); in Eagles Minimum Essential Medium (MEM) with 1 µg/mL penicillin, 1 µg/mL streptomycin, and 10% FBS; in a 1:1 mixture of MEM and F12 medium with 1 µg/mL penicillin, 1 µg/mL streptomycin, and 10% FBS. FAK and VEGFR3 expression were analyzed initially in six pancreatic cancer cell lines (all available from ATCC); the MiaPaCa-2 and Panc-1 cell lines were chosen for additional studies based on the high level of FAK expression and moderate level of VEGFR-3 expression. As a positive control, an MCF-7 cell line which naturally has high FAK expression and has been stably transfected to overexpress VEGFR3 was utilized. Melanoma cell lines A375 and C8161, MDA-MB231 breast carcinoma cell line, and the glioblastoma U87 cell line were purchased from ATCC. Cells were maintained in: Dulbecco's modified Eagle's medium supplemented with 10% fetal bovine serum (FBS) and 1 µg/ml penicillin-streptomycin for A375 and U87); in RPMI 1640 supplemented with 10% FBS, 1 µg/ml penicillin-streptomycin (for line C8161); DMEM:Ham's F12 (1:1 mixture) supplemented with 2 mM L-glutamine, 5% FBS and 1 µg/ml penicillin-streptomycin (for MDA MB231). U87 MG, DBTRG-O5MG (Denver Brain Tumor Research Group 05), U251 and GL261 brain cancer cell lines are available from ATCC. References relating to their use are available from ATCC.

Antibodies and Reagents.

Antibodies used for Western blotting were as follows. Phospho-specific VEGFR-3 antibody (pc460, rabbit polyclonal) was from Calbiochem (EMD Biosciences, San Diego, Calif.). Antibodies for VEGFR-3 were either from Millipore (MAB3757, clone 9D9F9, Millipore, Billerica, Mass.) or Santa Cruz (sc-321, rabbit polyclonal, Santa Cruz Biotechnology, Inc., Santa Cruz, Calif.). Monoclonal antibody for total poly (ADP-ribose) polymerase (PARP, 611038) was from BD Transduction Laboratories (BD Pharmingen, San Diego, Calif.). Monoclonal anti-FAK (4.47) and rabbit polyclonal anti-phospho-FAK (Y397) antibodies were obtained from Millipore (05-537), and Invitrogen (4624G, Invitrogen Corp., Carlsbad, Calif.), respectively. GAPDH and β-actin antibodies were from Santa Cruz.

RNA Isolation.

The untreated and treated cells were used for isolation of RNA. Total RNA from the frozen cell pellets were prepared using the RNeasy midi kits (Qiagen, Inc.) following manufacturer's instructions. Before labeling, RNA samples were quantitated using a ND-1000 spectrophotometer (Nano-Drop).

RT-PCR.

Total cellular RNA is extracted utilizing the RNA-Easy Kit (Qiagen, Valencia, Calif.) according to manufacturer's instructions. For the first strand synthesis of cDNA, 5 µg of RNA is used in a 20 µL reaction mixture utilizing a cDNA Cycle Kit (Invitrogen) according to the supplier's instructions. Resulting reverse transcription products are diluted ten times and stored at −20° C. until later use. PCR amplification is done with 100 ng of cDNA. The 784 bp VEGFR-3 fragment is amplified using primers forward 5'-GAAAGTGCATCCA-CAGAGACC-3' and reverse 5'-TCTATGCCTGCTCTC-TATCTG-3', at cycling conditions 34 cycles; 94° C. for 45 sec, 56° C. for 45 sec, and 72° C. for 1.5 min. GAPDH is utilized as an internal control. The GAPDH fragment is amplified under the same conditions using primers forward 5'-GAAGGTGAAGGTCGGAGTC-3', and reverse 5'-GAA-GATGGTGATGGGATTTC-3'. Experiments are repeated at least three times.

Immunoprecipitation and Western Blotting.

For immunoprecipitation, cells are lysed with NP40 lysis buffer, and 1000 µg of total protein is precleared with protein A/G-agarose beads (CalBiochem) at 4° C. for 1 hour and then incubated with 5 µg of antibody overnight followed by a 2 hour incubation with protein A/G-agarose beads at 4° C. Precipitates are washed thrice with cold PBS and the beads are resuspended in SDS-PAGE sample loading buffer, boiled for 5 minutes, and resolved by SDS-PAGE. Proteins are transferred to polyvinylidene difluoride membrane, probed with the appropriate antibody, and detected with chemiluminescence using Amersham ECL Western blotting detection reagents (GE Healthcare Life Sciences, Piscataway, N.J.).

Western blots were performed essentially as previously described. See: Beierle E, Ma X, Trujillo A, Kurenova E, Cance W, Golubovskaya V: Inhibition of focal adhesion kinase and src increases detachment and apoptosis in human neuroblastoma cell lines. *Mol Carcinog* 2010, 49:224-234; Kurenova E, Xu L, Yang X, Baldwin A J, Craven R, Hanks S, Liu Z, Cance W: Focal adhesion kinase suppresses apoptosis by binding to the death domain of receptor-interacting protein. *Mol Cell Biol* 2004, 24:4361-4371. Briefly, cells were treated with the agent under study, then lysed on ice for 30 min in a buffer containing 50 mM Tris-HCL, (pH 7.5), 150 mM NaCl, 1% Triton-X, 0.5% NaDOC, 0.1% SDS, 5 mM EDTA, 50 mM NaF, 1 mM NaVO$_3$, 10% glycerol, and protease inhibitors: 10 µg/mL leupeptin, 10 µg/mL PMSF and 1 µg/ML aprotinin. The lysates were cleared by centrifugation at 10 000 rpm for 30 min at 4° C. Protein concentrations were determined using a Bio-Rad kit (BioRad, Hercules, Calif.) and proteins were separated by electrophoresis on SDS-PAGE gels. Antibodies were used according to manufacturer's recommended conditions. Molecular weight markers were used to confirm the expected size of the target proteins. Immunoblots were developed with chemiluminescence Amersham ECL Western blotting detection reagents (GE Healthcare Biosciences). Blots were stripped with stripping solution (Bio-Rad) at 37° C. for 15 minutes and then reprobed with selected antibodies. Immunoblotting with antibody to β-actin or GAPDH provided an internal control for equal protein loading.

Example 6

Cell Viability Assays

Equal numbers of cells were plated and allowed to attach for 24 hours. Cells were treated with the drug or control as described. Cellular viability was measured using trypan blue exclusion and cell counting with a hemacytometer. Viability was further measured with an MTS (3-(4,5-dimethylthiazol-2-yl)-5-(3-carboxymethoxyphenyl)-2-(4-sulfophenyl)-2H-tetrazolium) assay. MTS in the presence of phenazine methosulfate (PMS), produces a formazan product that has an absorbance maximum at 490-500 nm in phosphate-buffered saline. In brief, cells were plated at 5×10$^3$ cells per well on 96-well culture plates and allowed to attach. Following treatment with siRNA or peptides, 20 µg of MTS was added to each well and the absorbance at 490 nm was measured using a kinetic microplate reader (V$_{max}$, Molecular Devices, Inc., Sunnyvale, Calif.). The MTS assay was performed at 72 hours after exposure of the cells to determine the IC$_{50}$ for each of the selected compounds.

Example 7

Binding Assay

We used a label-free OctetRED method for determining kinetic constants for the binding of small molecule inhibitors to the FAK FAT domain.

Example 8

Clonogenicity

The 500-1000 cells were plated on 6 well plates and incubated at 37° C. for 1-2 weeks. Then cells were fixed in 25% methanol and stained with Crystal Violet and colonies were visualized and counted in two independent experiments.

Figure 11:
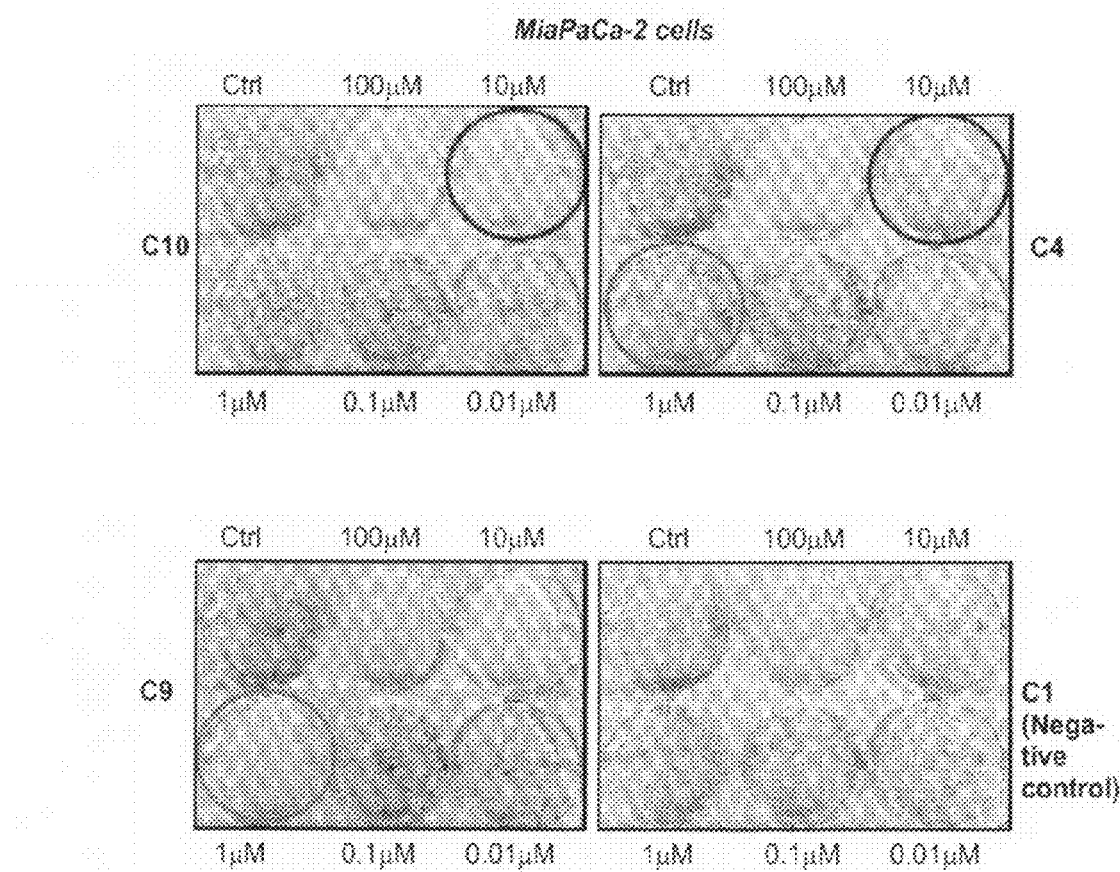
FIG. 11. shows the inhibitory effects of compounds C9 and C10 on colony formation of pancreatic cancer cells.

In FIG. 11, results of such a clonogenicity study are shown for compounds C9 and C10 using a pancreatic cancer cell line. In this particular study, since compound C1 is not active against this particular cancer cell line (see FIG. 3), it was used as a negative control. Chloropyramine ("C4"), which has been previously shown to have some activity against this cancer cell line, was used as a positive control. In this study, both C9 and C10 are active at much lower doses than C4 (compare the plates in the red and blue circles).

Example 9

Cellular Detachment Assay

Equal numbers of cells were plated and allowed to attach for 24 hours. The cells were then treated as described. Detached and adherent cells were collected separately and counted with a hemacytometer. The percentage of detached cells was determined (detached/attached+detached×100) and reported as change in percent detached cells.

Example 10

Apoptosis Assays

Apoptosis was determined by two methods. Following treatment with the drug, cells were stained with Hoechst 33258 as previously described [30, 31]. Cells undergoing apoptosis have condensation and fragmentation of nuclei. Hoechst stain binds to DNA and demonstrates condensed chromatin or micronuclei in cells that are undergoing apoptosis. All cells, both floating and adherent were harvested, fixed to a glass slide, stained with Hoechst 33258, positive cells counted with fluorescence microscopy, and a percentage of apoptotic cells were calculated in three independent fields with 100 nuclei per field. It also was performed by flow cytometry with TUNEL assay Apoptosis was also detected by immunoblotting for total PARP and Caspase 3 expression. During apoptosis, poly (ADP-ribose) polymerase (PARP) and Casp 3 are cleaved. The disappearance of the total as detected by immunoblotting is a method that can be utilized to detect apoptosis. Cells were treated as described, lysates were collected, and immunoblotting was performed. Bands were detected by chemiluminescence and β-actin or GAPDH served as an internal control.

Example 11

Invasion

Invasion assay was performed with cell invasion kit from Chemicon International Inc. The cell invasion assay was performed on 24 well plates using Boyden chambers, coated with extracellular matrix, ECMatrix according the company protocol. The invaded cells through the chamber pores were stained in the staining solution and collected in 10% acetic acid. The staining was processed by colorimetric reading at 560 nm.

Example 12

Tumor Growth in Xenograft Nude Mice

Female nude or SCID mice were purchased six weeks old and were maintained in the animal facility, and all experiments were performed in compliance with NIH animal use guidelines using IACUC protocol approved by the Roswell Park Animal Care Committee. The $1\times10^6$ MiaPaCa2 cells were injected into mice subcutaneously. Next day after cell injection or week later, when tumor size reached 100 mm$^3$, drug was introduced by IP or gavage orally daily, 5 days per week for several weeks. Tumor diameters were measured with calipers and tumor volume in mm$^3$ was calculated using this formula: tumor volume=(width)$^2\times$Length/2. At the end of the experiment, tumor weight and volume were determined. Tumor samples were collected for Western blotting and for immunohistochemical analysis.

Use of Compound 9A, 9B or C10 at various concentrations.

Figure 6A:
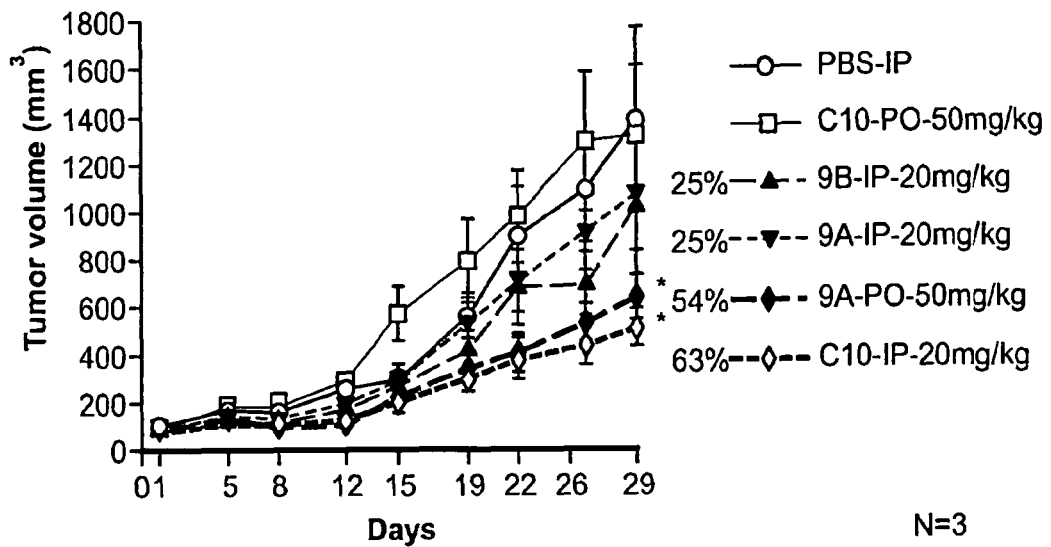
FIG. 6A shows relative efficacy in reducing tumor volume.
Figure 6B:
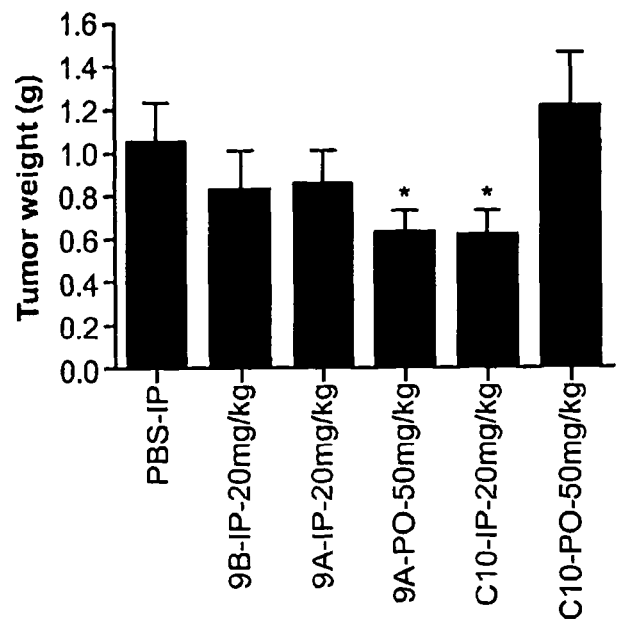
FIG. 6B shows relative efficacy in reducing tumor weight. "PBS-IP" is the control treatment group; PO=per oral (oral gavage); IP=intraperitoneal injection FIG. 7. shows a comparison of the efficacies of Compound 9 ("C9") and chloropyramine ("C4") on tumor growth in xenografted nude mice.

FIG. 6 demonstrates the results of experiments wherein $1\times10^6$ MiaPaCa-2-luc cells were subcutaneously inoculated into the right flank of mice. Mice received a daily dose of the indicated amount of compounds 9A, 9B or C10 either by intraperitoneal injection (IP) or by oral gavage (PO). Treatment was initiated after tumors reached a volume of approximately 100 mm$^3$. Statistically significant differences (* P<0.05) in mice treated with compound 9A-PO-50 mg/kg or compound C10-IP-20 mg/kg, as compared to vehicle(PBS)-treated tumors were observed (FIG. 6A). The percent reduction in tumor volume compared to the control group ("PBS-IP") is indicated in FIG. 6B for each treatment group. Mice did not show a statistically significant weight loss in any of the treatment groups.

Comparison of C9 with Chloropyramine.

Figure 7A:
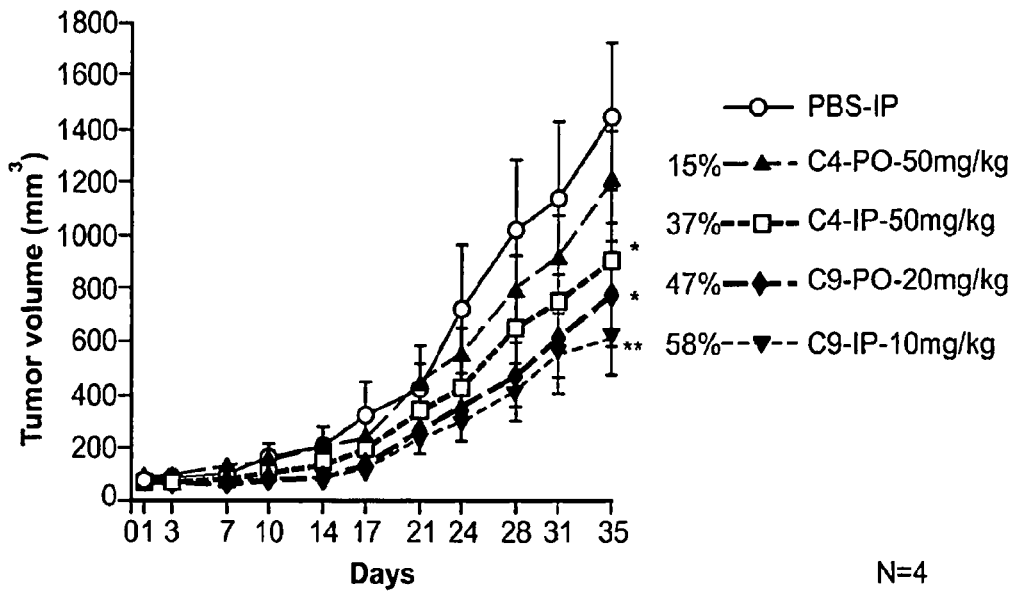
FIG. 7A shows relative efficacy in reducing tumor volume.
Figure 7B:
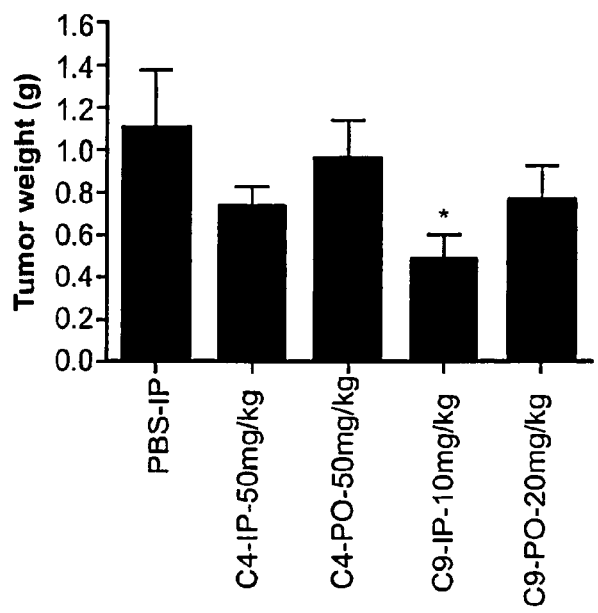
FIG. 7B shows relative efficacy in reducing tumor weight. "PBS-IP" is the control treatment group; PO=per oral (oral gavage); IP=intraperitoneal injection FIG. 8. provides data from a comparative study on tumor growth in xenografted nude mice. PO=per oral (oral gavage); IP=intraperitoneal injection.

FIG. 7 presents the results of experiments wherein mice received a daily dose of the indicated amount of C9 or chloropyramine (designated "C4" in this figure and used as a positive control). Treatment was initiated after tumors reached a volume of approximately 100 mm$^3$. Statistically significant differences for C4 delivered intraperitoneally at 50 mg/kg (*P<0.05, "C4-IP-50 mg/kg"), and C9 delivered intraperitoneally at a five-times lower dose, i.e. 10 mg/kg ((**P<0.01, "C9-IP-10 mg/kg"), as compared to vehicle (PBS)-treated tumors, were observed in the treated mice. The percent reduction in tumor volume compared to control PBS-IP group is indicated in the figure for each treatment group. Mice did not show statistically significant weight loss in any of the treatment groups.

Use of C9 in Combination with Gemcitabine.

Figure 8A:
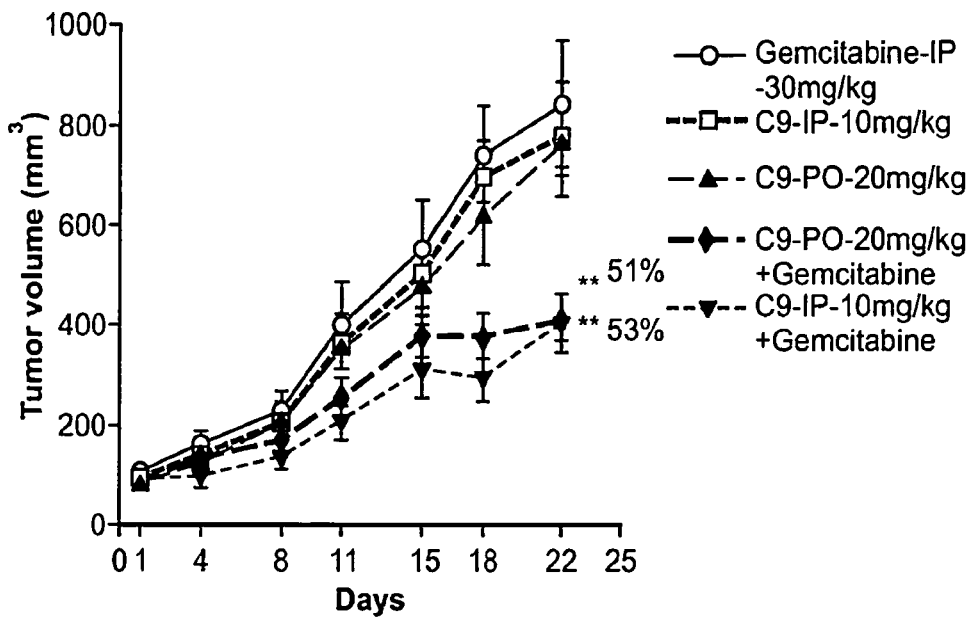
FIG. 8A shows the efficacy of Compound 9 administered either alone or in combination with gemcitabine in reducing tumor volume.

FIG. 8 demonstrates the results of experiments wherein mice received a daily dose of the indicated C9, C9 and gemcitabine, or gemcitabine alone. Treatment was initiated after tumors reached a volume of approximately 100 mm$^3$. Statistically significant reductions in tumor burden was seen in mice treated with the combination therapy of C9-IP and gemcitabine or C9-PO and gemcitabine (**P<0.01) when compared to single drug therapy (see FIG. 8A). The percent reduction in tumor volume as compared to the gemcitabine treatment group is indicated for each treatment group. Mice did not show statistically significant weight loss in any of the treatment groups.

Figure 8B:
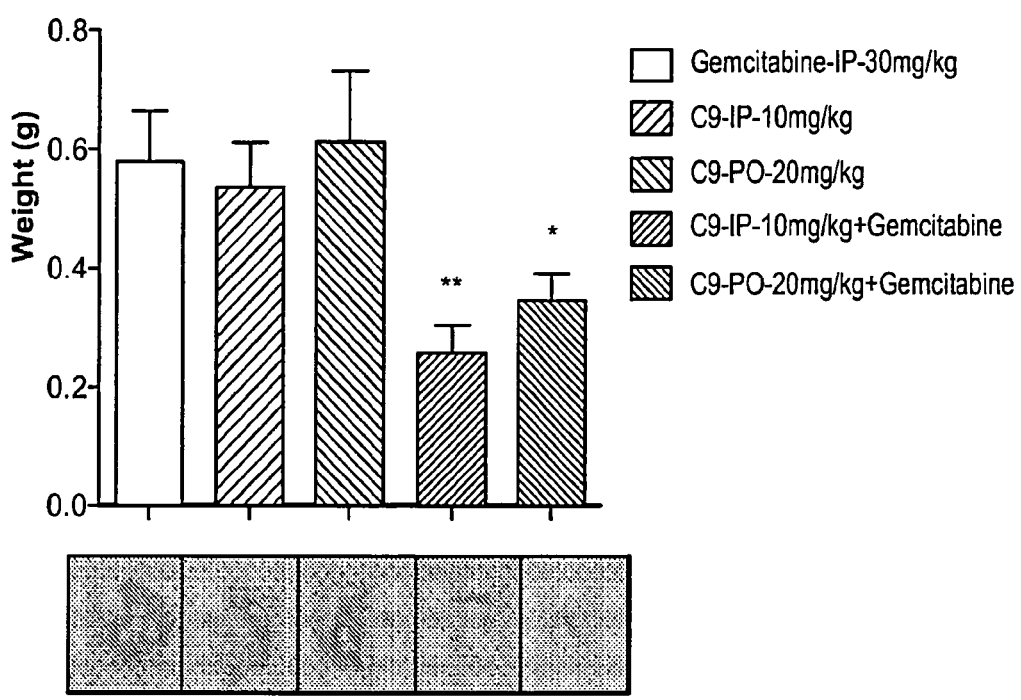
FIG. 8B shows the efficacy of Compound 9 administered either alone or in combination with gemcitabine in reducing tumor weight.

FIG. 8B presents the tumor weights following sacrifice of the mice studied in FIG. 8A. Statistically significant reductions in tumor weight were seen in mice treated with the combination of C9-IP and gemcitabine (**P<0.01) or C9-PO and gemcitabine (*P<0.05) as compared to treatment with gemcitabine or C9 alone.

Figure 8C:
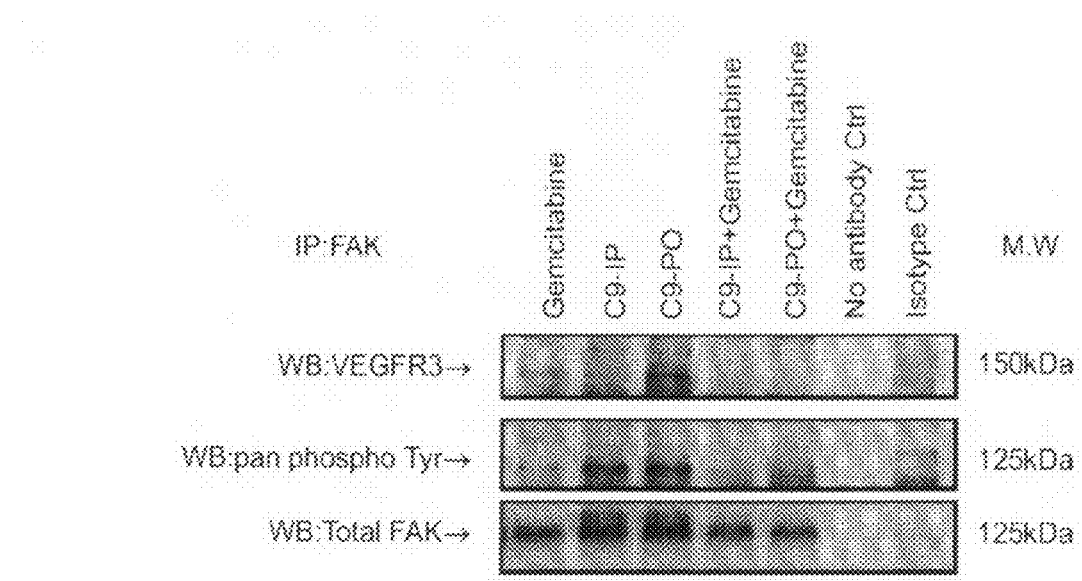
FIG. 8C shows the efficacy of Compound 9 either alone or in combination with gemcitabine in disrupting the binding of FAK and VEGFR3 (Flt-4) proteins and reducing the tyrosine phosphorylation of FAK. IP:FAK=Immunoprecipitation of FAK; WB=Western blot; MW=molecular weight.

In FIG. 8C, the biggest tumors from each treatment group in FIG. 8B were selected and prepared for immunoprecipitation with FAK antibody following the indicated treatment. Treatment with C9-IP alone and treatment with the combination of C9-IP and gemcitabine or C9-PO and gemcitabine disrupted binding of FAK and VEGFR3 (Flt-4) proteins. Treatment with C9 and gemcitabine reduced tyrosine phosphorylation of FAK.

Example 13

Endpoints of Anti-Tumor Efficacy Include 1) differences in tumor size between treated and control animals at termination of the experiment (T/C % and T–C4anal/T–C4%) and 2) differences in blood vessels density and lymphatic vessels density. One hour following the last dose, tumor tissue were snap frozen and Erk1/2, Akt, FAK and VEGFR-3 phosphorylation, as well as total protein levels (to ensure equal loading), were determined ex vivo by Western blot. Tumor tissues were sectioned and stained for total and phosphorylated FAK and VEGFR-3 in addition to TUNEL staining (apoptosis), Ki67 (proliferation), CD31 (angiogenesis) and LYVE1 (lymphangiogenesis). Necropsy was performed to evaluate drug toxicity.

Data Analysis.

Experiments were repeated at least in triplicate, and data were reported as mean±standard error of the mean. An ANOVA or student's t-test was used as appropriate to compare data between groups. Statistical significance was determined at P<0.05.

Example 14

Results (A) Inhibition of the Growth of Selected Cancer Cell Lines

Figure 2:
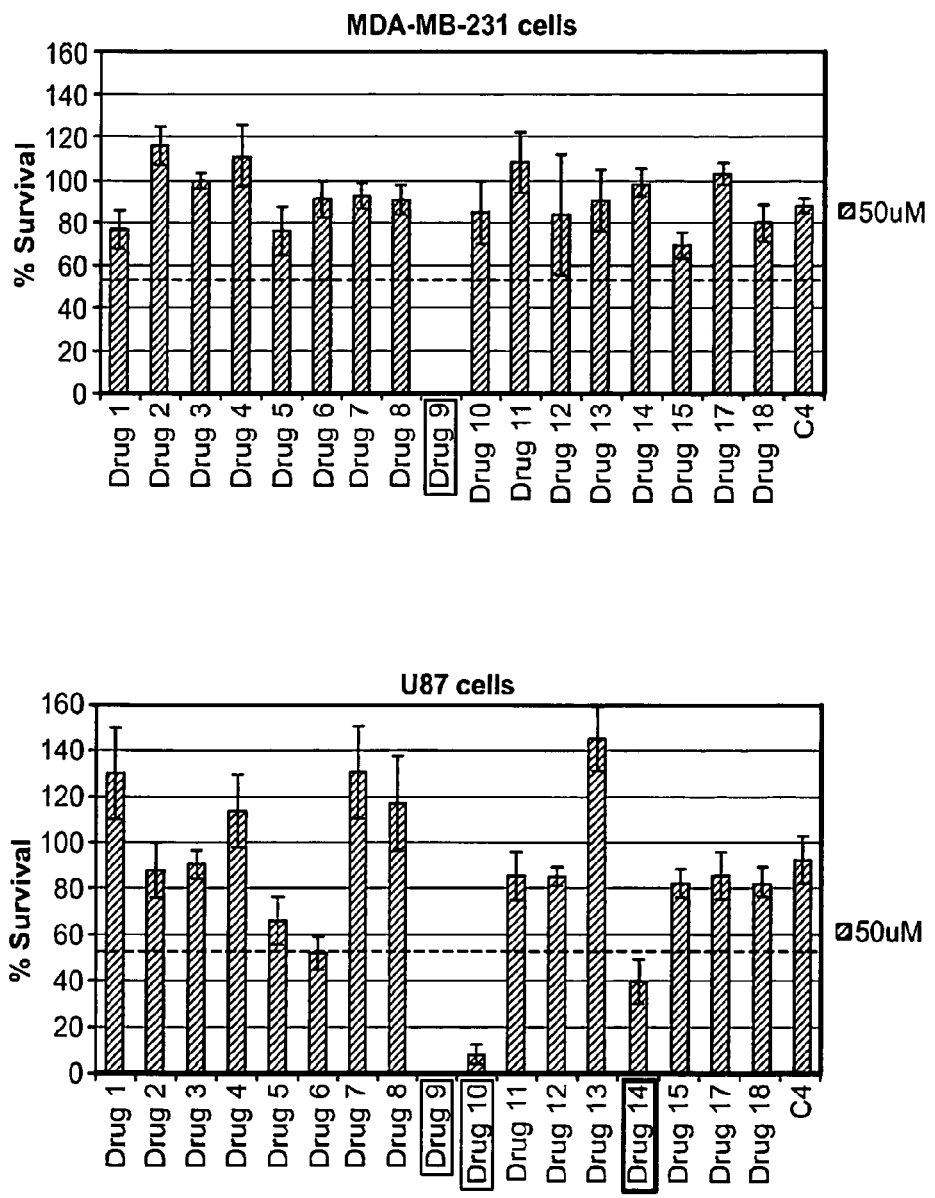
FIG. 2. depicts the effect of compounds of the invention on viability of breast cancer and glioblastoma cells FIG. 3. depicts the effect of compounds of the invention on pancreatic cancer cells FIG. 4. depicts the effect of compound 9 of the invention in combination with gemcitabine FIG. 5. depicts the effect of compound 9 of the invention on DBTRG cells (brain cancer)
Figure 3:
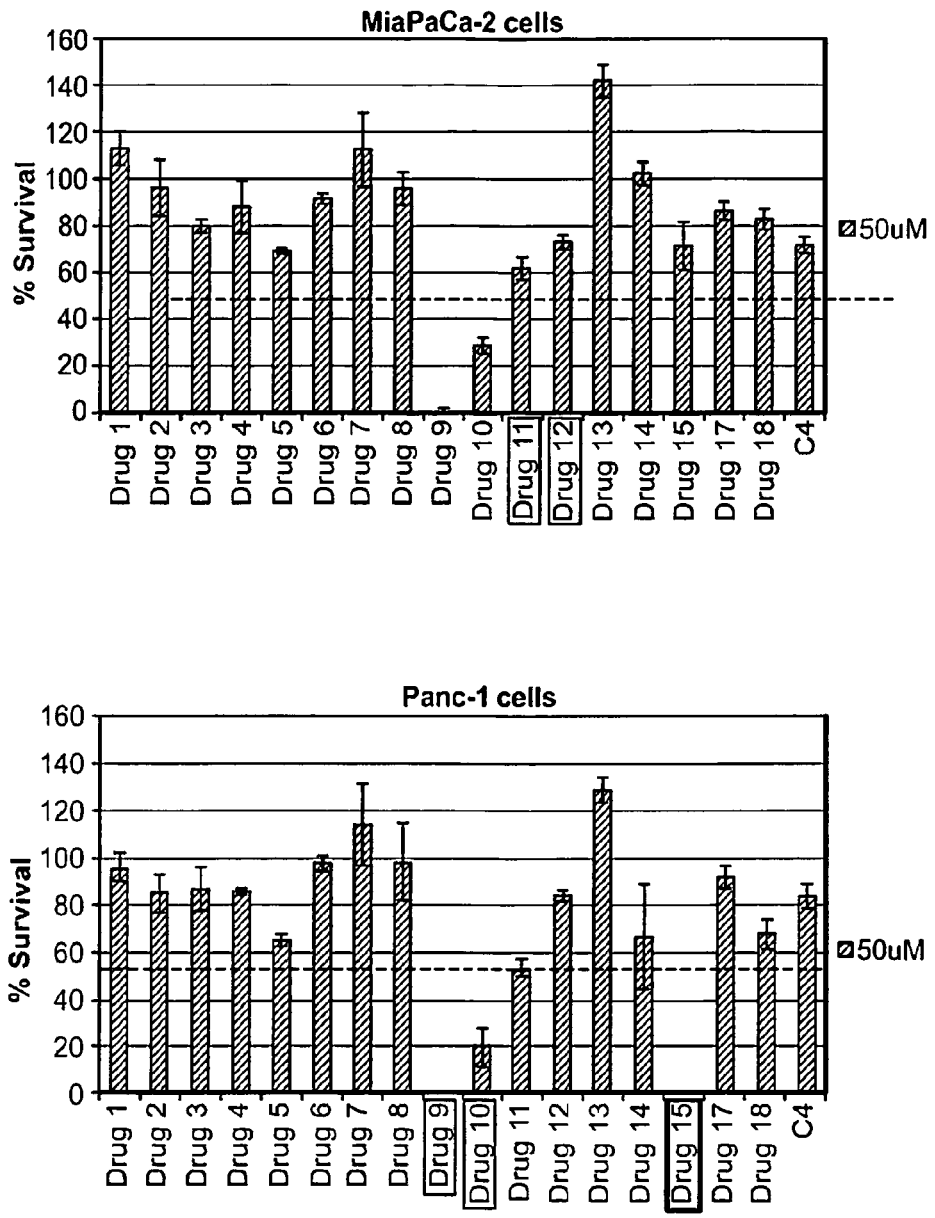

FIGS. 1-3 show the results of exposure of the indicated cancer cell lines to 50 μM of the indicated compounds of the invention.

Figures 9A, 9B:
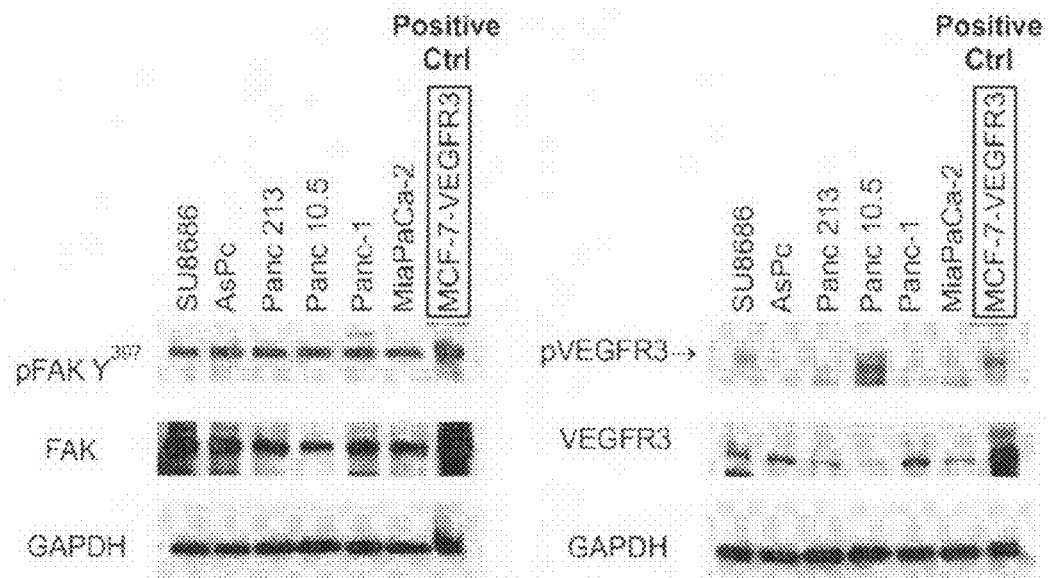
FIG. 9. shows the efficacy of compounds C9, 9A, 9B, and C10 on the viability of a panel of pancreatic cancer cell lines.
Figure 9C:
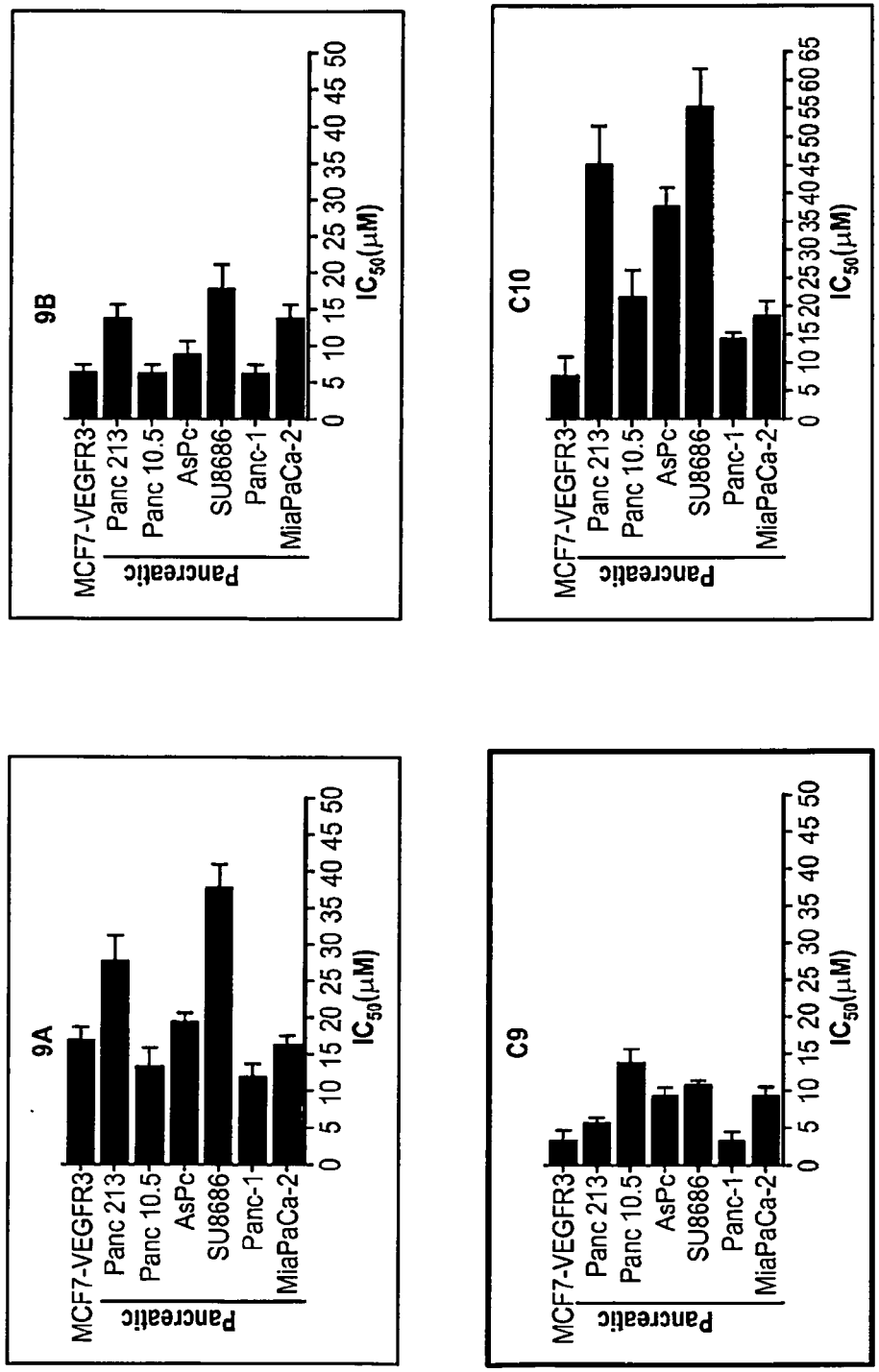

FIG. 9 shows the results of exposure of a panel of six different pancreatic cancer cell lines, two of which were also used in the experiments presented in FIG. 3, to four selected compounds of the invention. Western blots demonstrate that these cells all show robust expression of total FAK and moderate to high expression of VEGFR3, a binding target of FAK (upper panel). As a positive control, MCF-7 cells were transfected to overexpress VEGFR3. GAPDH serves as a loading control.

Figure 10:
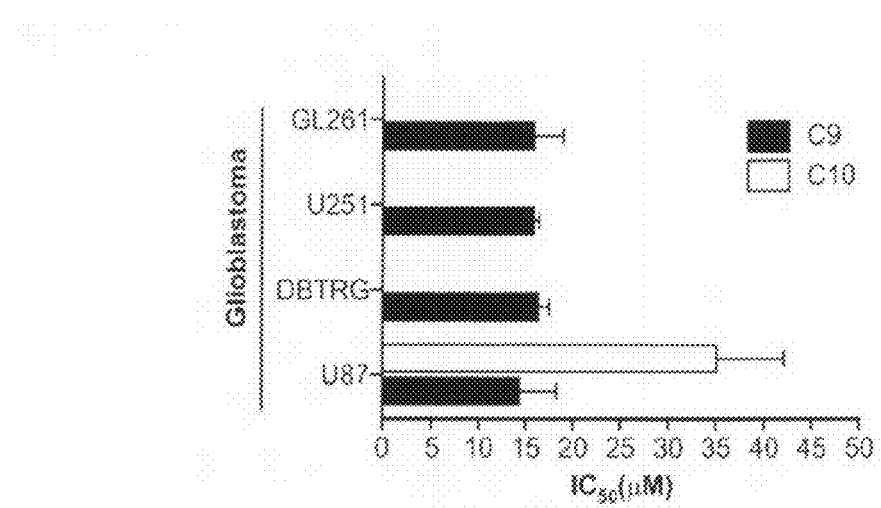
FIG. 10 shows the efficacy of compounds C9 and C10 on the viability of a various glioblastoma cell lines.

FIG. 10 demonstrates the efficacy of compounds C9 and C10 in inhibiting the viability of several gliobastoma cell lines, including GL251 and U251 which are available from ATCC. Glioblastoma, also known as grade 4 (IV) astrocytoma or glioblastoma multiforme. is a highly invasive cancer. Glioblastomas are tumors that arise from astrocytes—the star-shaped cells that make up the "glue-like," or supportive tissue of the brain. These tumors are usually highly malignant (cancerous) because the cells reproduce quickly and they are supported by a large network of blood vessels. The first step in treating glioblastoma is to relieve pressure on the brain and safely remove as much tumor as possible through surgery. Because glioblastomas have finger-like tentacles, they are very difficult to completely remove. This is particularly true when they are growing near the parts of the brain that control important functions such as language and coordination. Radiation and chemotherapy may be used to slow the growth of tumors that cannot be removed with surgery. Even if there has been adequate removal, the invasive nature and rapid proliferation of glioblastoma does not allow its control by conventional treatment protocols. For patients whose tumor location does not allow for tumor resection, they have then a limited survival. The clinical hallmarks of glioblastoma are its aggressive growth and inexorable recurrence despite multimodal therapy with surgery followed by radiation and temozolomide therapy. Unfortunately, current standard-of-care therapy results in a median survival of only 12-15 months. While 90%-95% of glioblastomas arise de novo and are considered "primary"; 5%-10% arise from lower grade gliomas in younger patients and are termed "secondary". It has been recognized that receptor tyrosine kinases (including EGFR, PDGFRA, and MET), the PI3K pathway, signaling pathways activated by PTEN and NF1 loss, and the mutant IDH proteins play central roles in the pathobiology of glioblastoma.

(B) Synergy with Gemcitabine

Figure 4A:
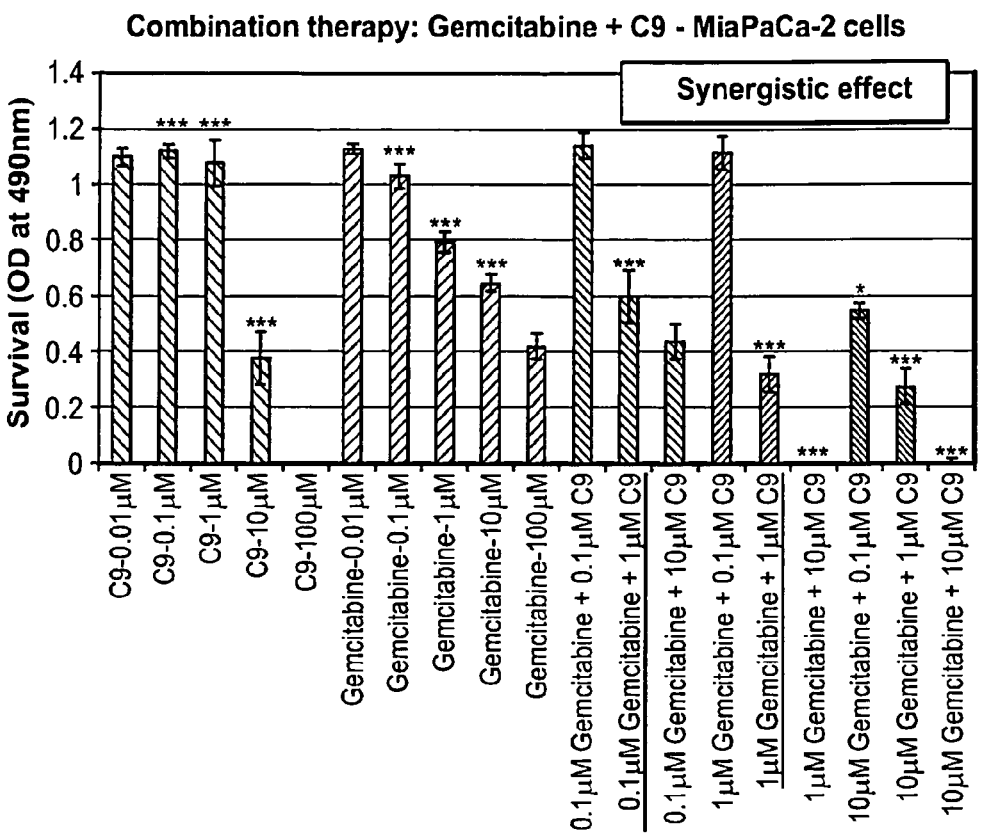
Figure 4B:
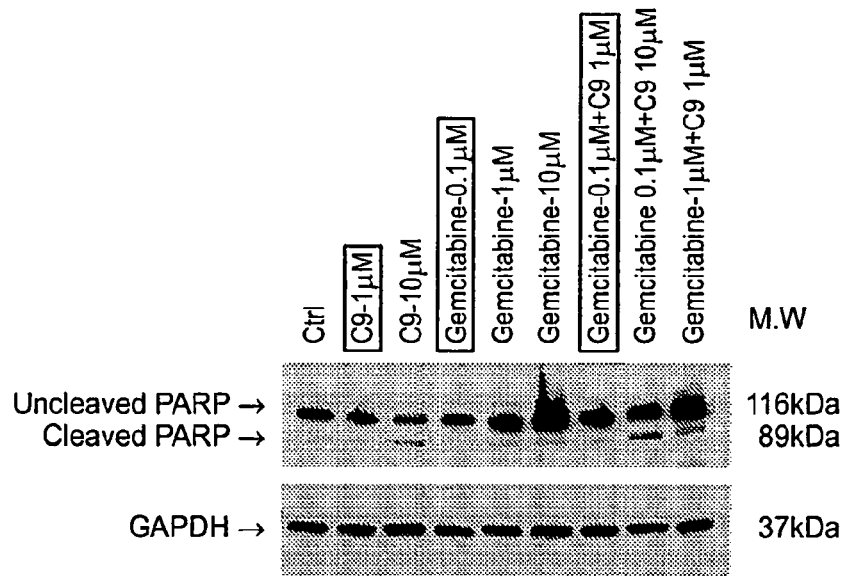
Figure 5:
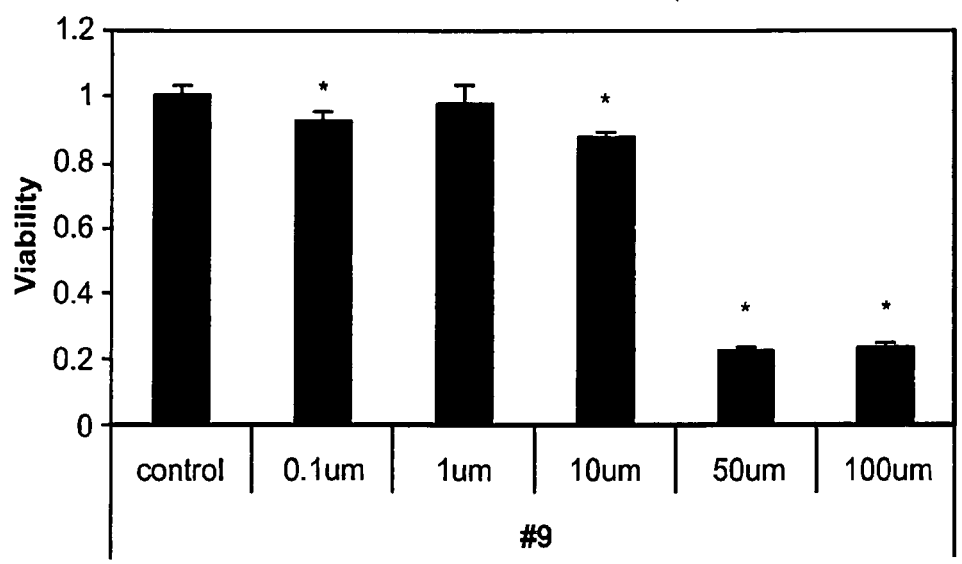

FIG. 4 shows the efficacy of Compound 9 in combination with gemcitabine in inhibiting the viability of pancreatic cancer cells. In FIG. 4A, the MTS viability assay was performed on MiaPaCa-2-luc cells, which were treated with Gemcitabine, C9 or Gemcitabine with C9 at the indicated concentrations. After 72 h, the MTS reagent was added and plates were read at 490 nm. Error bars denote ±SD, *P<0.05; **P<0.01. In FIG. 4B, MiaPaCa-2 cells were treated with C9 and Gemcitabine at the indicated concentrations for 24 h. Western blotting confirmed that combination treatment of C9 and Gemcitabine increased the PARP cleavage product. ENT1 levels also increased with combination treatment as compared to cells treated with gemcitabine alone treated cells. GAPDH serves as a loading control.

Figure 14:
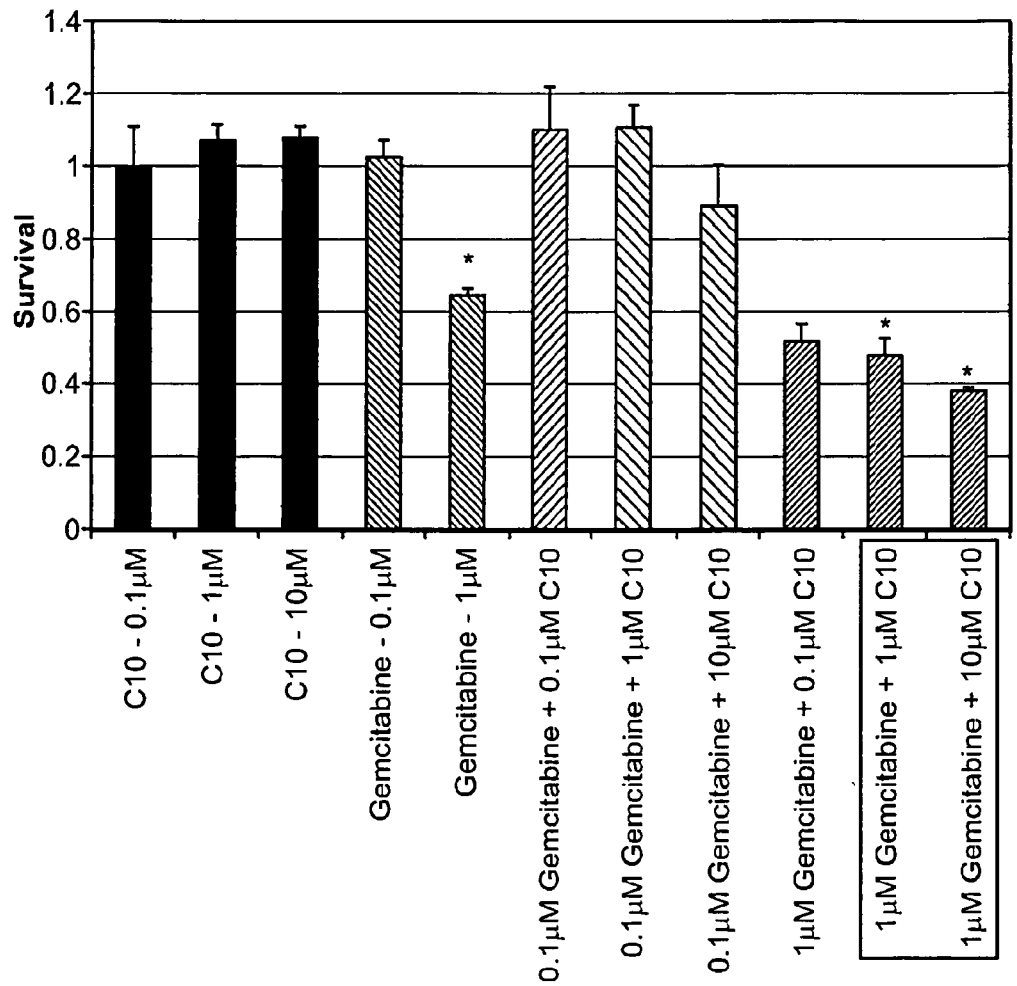
FIG. 14. shows the synergy of C10 and gemcitabine on the viability of the MiaPaCa-2 pancreatic cancer cell line.

FIG. 14 shows the efficacy of Compound 10 in combination with gemcitabine in inhibiting the viability of pancreatic cancer cells. The MTS viability assay was performed on MiaPaCa-2-luc cells, which were treated with Gemcitabine, C10 or Gemcitabine with C10 at the indicated concentrations. After 72 h, the MTS reagent was added and plates were read at 490 nm. Error bars denote ±SD, *P<0.05; **P<0.01.

Figure 12:
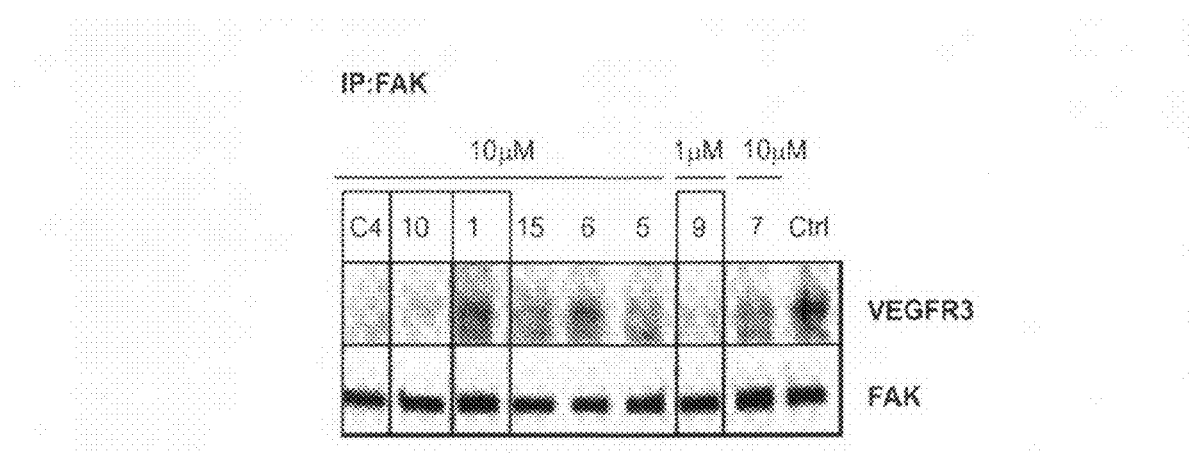
FIG. 12. shows the specificity of C9 and C10 in disrupting FAK-VEGFR3 binding.

(C) Demonstration of FAK Binding and Target Specificity by Compounds of the Invention FIG. 12 shows the results of a study of MiaPaCa-2 cells which were treated with different amounts of either C9 or C10. The study utilized the "Octet Red" technology (Forte-Bio, Menlo Park, Calif.), which provides real-time monitoring for protein-small molecule interactions and binding events using BioLayer Interferometry (BLI) technology. Any change in the number of molecules bound to the biosensor tip changes the optical layer thickness. Immunoprecipitation with FAK antibody after 24 h of treatment of MiaPaCa-2 cells revealed that C9 at 1 µM and C10 at 10 µM disrupted binding of FAK and VEGFR3 (Flt-4) proteins. Since C1 is not active against this pancreatic cancer cell line, it was included as a negative control, and chloropyramine ("C4"), which has been shown previously to be active against this cell line, was used as a positive control.

(D) Modeling of Compounds of the Invention in Disrupting FAK-VEGFR3 Binding

Figure 13:
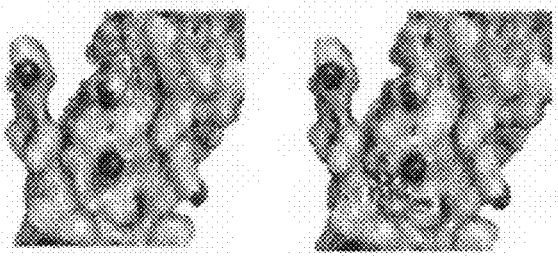
FIG. 13. shows the binding of C9 and C10 to the FAT domain of FAK.
Figure 13:
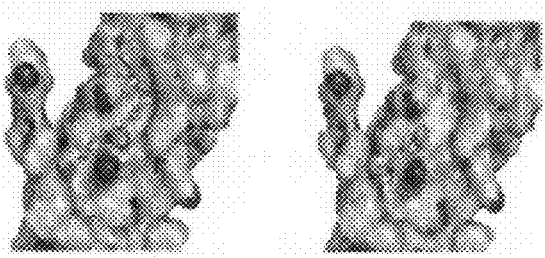

In FIG. 13, a computer-modeling study of the ability of the compounds of the invention to disrupt FAK-VEGFR3 binding through the FAT domain of FAK is demonstrated. A label-free OctetRED method was used for determining kinetic constants for the binding of C9 or C10 to the FAK-FAT domain. Label-free analysis of the association and dissociation of a small molecule with the target protein of interest results in the determination of kinetic constants including the association rate constant (ka), dissociation rate constant (kd), and equilibrium dissociation constant (KD). Analysis of chloropyramine ("C4") is provided, as well as C1, which does not appear to bind to the FAT domain.

Figure 15:
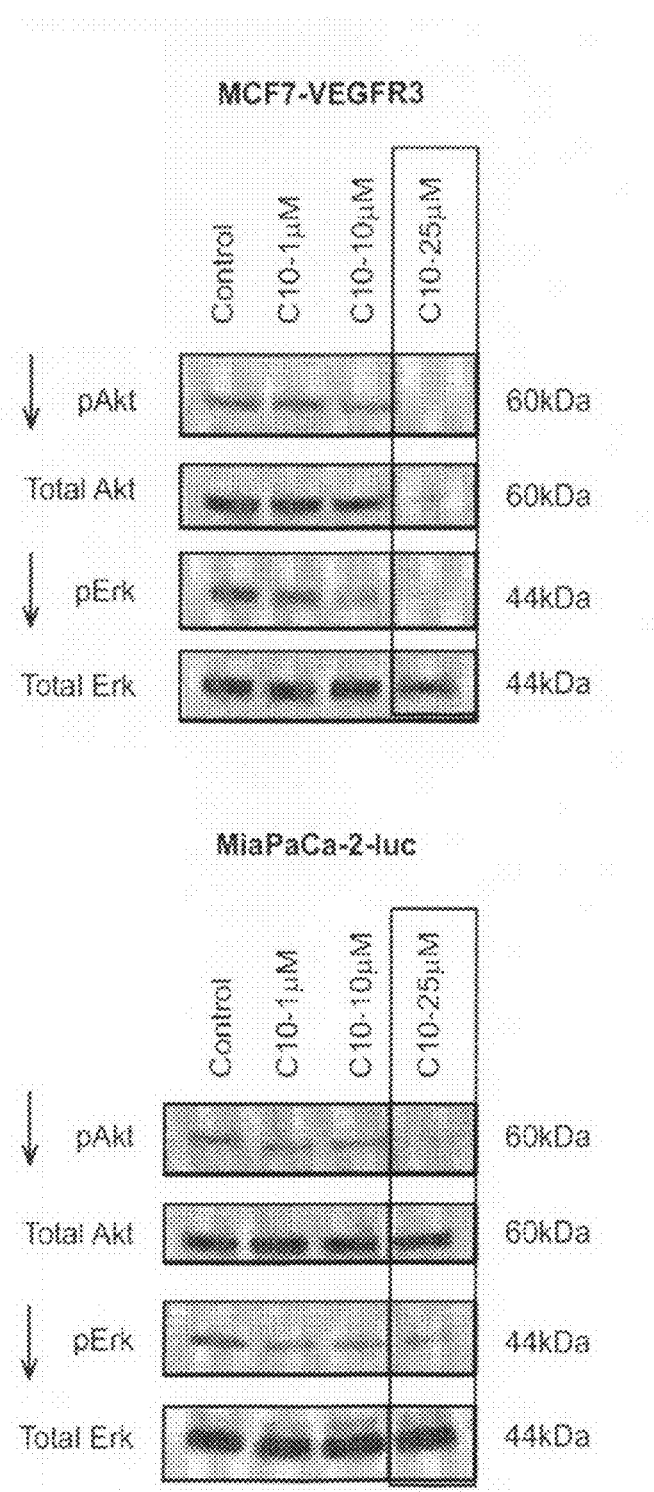
FIG. 15. shows the effect of C10 on downstream effectors of FAK inhibition.
Figure 16:
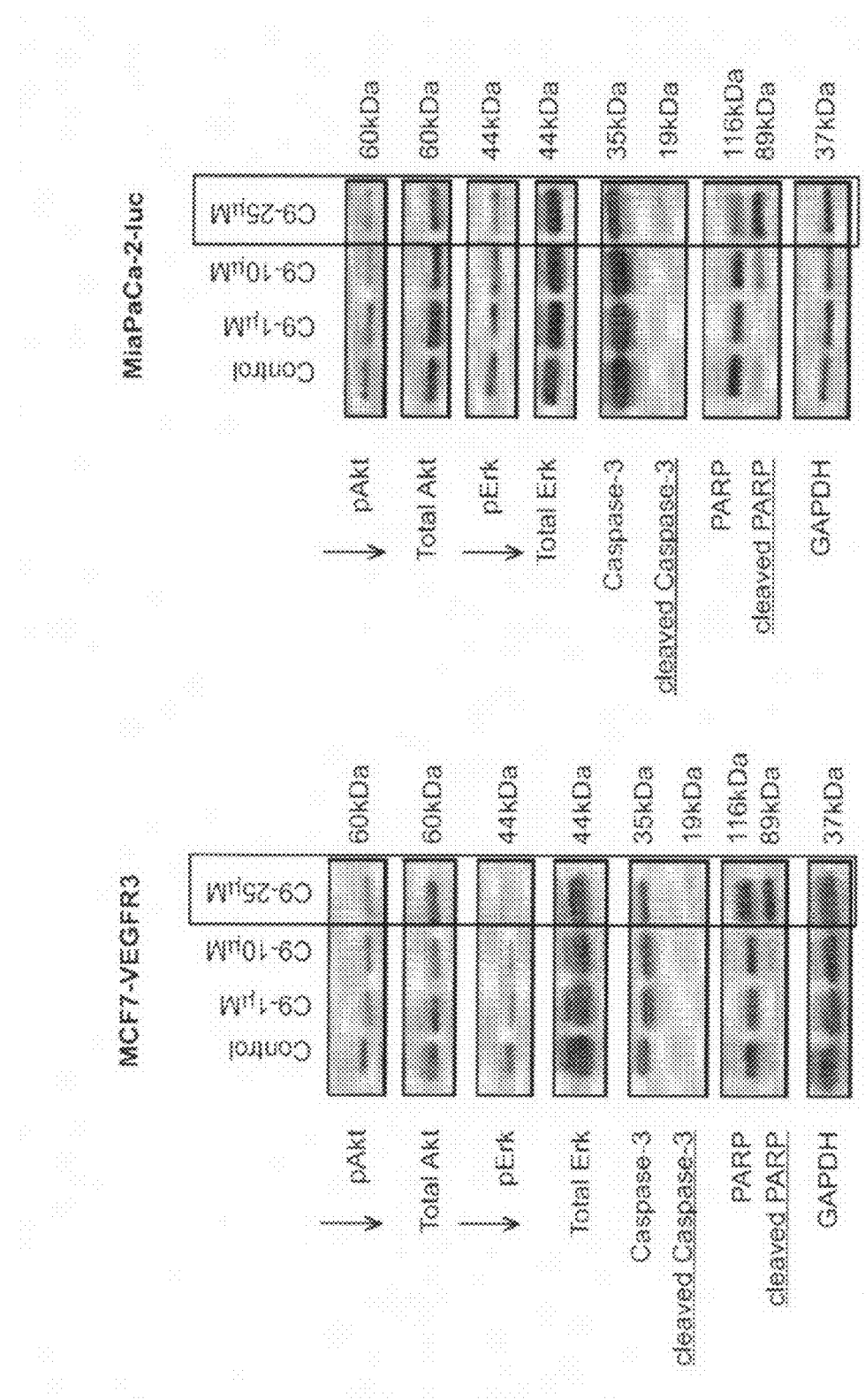
FIG. 16. shows the effect of C9 on downstream effectors of FAK inhibition and apoptosis.

(E) Studies on the Effect of Compounds of the Invention on Activities of Downstream Effectors in the FAK-Triggered Cascade and Apoptosis In FIGS. 15 and 16, MiaPaCa-2-luc cells (with an $IC_{50}$ for C9 of 8 µM and for C10 of 20 µM) and MCF-7-VEGFR3 cells (with an $IC_{50}$ for C9 of 4 µM and for C10 of 8 µM) were treated with 1, 10 or 25 µM C9 or C10 for 24 hours (the MCF-7-VEGFR3 cells serving as a positive control in this study). Western blots were performed as described above to determine the levels of total Akt, phosphorylated Akt (pAkt), total Erk, and phosphorylated Erk (pErk). This study confirmed that both C9 and C10 induced strong down-regulation of phosphorylated Akt and phosphorylated Erk. As shown in FIG. 16, the C9 treated cells were further assayed for apoptotic activity. C9 caused apoptosis in both cancer cell lines, as demonstrated by PARP cleavage and Caspase 3 activation. In both figures, GAPDH serves as a loading control.

Figure 17:
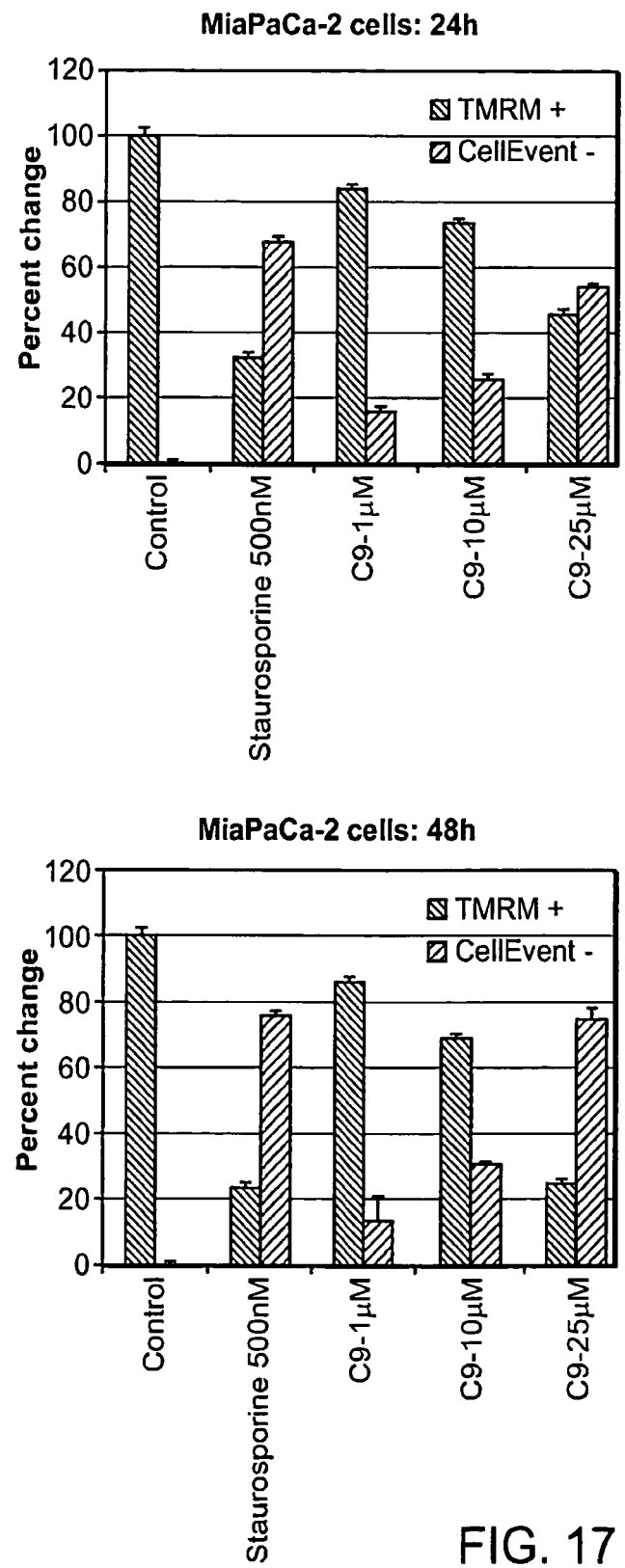
FIG. 17. shows the effect of C9 on cell apoptosis.

In FIG. 17, the effect of C9 on apoptosis of pancreatic cancer cells is demonstrated by using (i) tetramethylrhodamine, methyl ester (TMRM), a cell-permeant, cationic, red-orange fluorescent dye that is readily sequestered by active mitochondria, and (ii) the CellEvent® Caspase-3/7 Green Detection Reagent, a fluorogenic substrate for activated caspase-3/7 which is compatible with both live cell and fixed cell imaging, with an absorption/emission maxima ~502/530 nm. Activation of caspase-3 is considered an essential event during apoptosis, making this an optimized reagent for analysis of apoptotic cells.

CellEvent Staining Protocol

The CellEvent reagent is a four amino acid peptide (DEVD), conjugated to a nucleic acid binding dye. The DEVD peptide sequence is a cleavage site for caspase-3/7 and the conjugated dye is non-fluorescent until cleaved from the peptide and bound to DNA. As cells to which the DEVD peptide has been added become apoptotic and the activation of caspase-3/7 occurs, the DEVD peptide is cleaved enabling the dye to bind to DNA and produce a bright, fluorogenic response. The fluorescence emission of the dye when bound to DNA is ~530 nm and can be observed using a standard "FITC" filter set.

The CellEvent™ Caspase-3/7 Green Detection Reagent was added at a final concentration of 5 µM to the treated cells and incubated for 30 minutes at 37° C. Cells were preserved with 3.7% formaldehyde for 15 minutes. Cells were also stained with tetramethylrhodamine, methyl ester (TMRM), a cell-permeant, cationic, red-orange fluorescent dye that is readily sequestered by active mitochondria. Cells were imaged using the FITC filter sets for CellEvent visualization and the rhodamine filter for TMRM visualization.

Results of these studies are presented in FIG. 17. An increase in the readout at 530 nm indicates an increasing number of apoptotic cells (green bars; "Cell Event"); a decrease in the number of cells containing the TMRM dye indicates a decrease in viability (red bars; "TMRM"). Staurosporine is used a positive control for cell apoptosis.

REFERENCES

1. Xu, L. H., et al., *Attenuation of the expression of the focal adhesion kinase induces apoptosis in tumor cells*. Cell Growth Differ, 1996. 7(4): p. 413-8.
2. McLean, G. W., et al., *The role of focal-adhesion kinase in cancer—a new therapeutic opportunity*. Nat Rev Cancer, 2005. 5(7): p. 505-15.

3. van Nimwegen, M. J. and B. van de Water, *Focal adhesion kinase: A potential target in cancer therapy.* Biochem Pharmacol, 2006.
4. Weiner, T. M., et al., *Expression of focal adhesion kinase gene and invasive cancer.* Lancet, 1993. 342(8878): p. 1024-5.
5. Owens, L. V., et al., *Overexpression of the focal adhesion kinase (p125FAK) in invasive human tumors.* Cancer Research, 1995. 55(13): p. 2752-5.
6. Golubovskaya, V. M., R. Finch, and W. G. Cance, *Direct interaction of the N-terminal domain of focal adhesion kinase with the N-terminal transactivation domain of p53.* J Biol Chem, 2005. 280(26): p. 25008-21.
7. Garces, C. A., et al., *Vascular endothelial growth factor receptor-3 and focal adhesion kinase bind and suppress apoptosis in breast cancer cells.* Cancer Res, 2006. 66(3): p. 1446-54.

The disclosures of each and every patent, patent application and publication cited herein are hereby incorporated herein by reference in their entirety.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A compound as follows:

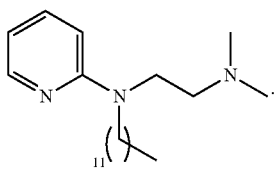

* * * * *